United States Patent
Swiss et al.

(10) Patent No.: US 11,186,827 B1
(45) Date of Patent: *Nov. 30, 2021

(54) GENETICALLY MODIFIED STEM CELLS

(71) Applicant: SDF BioPharma Inc., Rancho Santa Fe, CA (US)

(72) Inventors: Gerald F. Swiss, Rancho Santa Fe, CA (US); David Kiewlich, Alameda, CA (US)

(73) Assignee: SDF BIOPHARMA INC., Rancho Santa Fe, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/222,833

(22) Filed: Apr. 5, 2021

Related U.S. Application Data

(63) Continuation of application No. 16/826,104, filed on Mar. 20, 2020, now Pat. No. 10,982,190, which is a continuation of application No. 16/370,606, filed on Mar. 29, 2019, now Pat. No. 10,696,950, which is a continuation of application No. 16/146,980, filed on Sep. 28, 2018, now abandoned.

(60) Provisional application No. 62/734,910, filed on Sep. 21, 2018, provisional application No. 62/719,975, filed on Aug. 20, 2018, provisional application No. 62/717,587, filed on Aug. 10, 2018, provisional application No. 62/696,603, filed on Jul. 11, 2018, provisional application No. 62/694,634, filed on Jul. 6, 2018, provisional application No. 62/662,651, filed on Apr. 25, 2018, provisional application No. 62/637,913, filed on Mar. 2, 2018, provisional application No. 62/568,117, filed on Oct. 4, 2017, provisional application No. 62/567,604, filed on Oct. 3, 2017.

(51) Int. Cl.
| | |
|---|---|
| *C12N 5/071* | (2010.01) |
| *A61P 3/10* | (2006.01) |
| *A61K 35/17* | (2015.01) |
| *C12N 5/0783* | (2010.01) |
| *C12N 5/0781* | (2010.01) |
| *A61K 35/39* | (2015.01) |
| *C07K 14/52* | (2006.01) |

(52) U.S. Cl.
CPC ............ *C12N 5/0676* (2013.01); *A61K 35/17* (2013.01); *A61K 35/39* (2013.01); *A61P 3/10* (2018.01); *C07K 14/522* (2013.01); *C12N 5/0635* (2013.01); *C12N 5/0638* (2013.01); *C12N 5/0646* (2013.01); *C12N 5/0686* (2013.01); *C12N 2501/998* (2013.01); *C12N 2502/11* (2013.01); *C12N 2502/99* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,756,084 A | 5/1998 | Honjo et al. |
| 6,448,054 B1 | 9/2002 | Poznansky et al. |
| 7,033,831 B2 | 4/2006 | Fisk et al. |
| 7,776,564 B2 | 8/2010 | Chu et al. |
| 8,268,620 B2 | 9/2012 | Thomson et al. |
| 8,546,140 B2 | 10/2013 | Mack et al. |
| 10,696,950 B2 | 6/2020 | Swiss et al. |
| 2003/0013646 A1 | 1/2003 | Habener et al. |
| 2004/0043040 A1 | 3/2004 | Dunussi-Joannopoulos |
| 2007/0258943 A1 | 11/2007 | Penn et al. |
| 2008/0213319 A1 | 9/2008 | Kang et al. |
| 2008/0300165 A1 | 12/2008 | Poznansky et al. |
| 2009/0280096 A1 | 11/2009 | Kubo et al. |
| 2011/0280842 A1 | 11/2011 | Melton et al. |
| 2012/0053119 A1 | 3/2012 | Habener et al. |
| 2013/0164787 A1 | 6/2013 | Agulnick et al. |
| 2013/0273651 A1 | 10/2013 | Gold et al. |
| 2016/0083693 A1 | 3/2016 | Xu et al. |
| 2016/0184234 A1 | 6/2016 | Poznansky et al. |
| 2017/0081641 A1 | 3/2017 | Deisher |
| 2017/0196913 A1 | 7/2017 | Ben-Porath et al. |
| 2017/0246250 A1 | 8/2017 | Poznansky et al. |
| 2019/0100729 A1 | 4/2019 | Kiewlich et al. |
| 2019/0100730 A1 | 4/2019 | Swiss et al. |
| 2020/0283731 A1 | 9/2020 | Swiss et al. |

FOREIGN PATENT DOCUMENTS

WO    WO-2012/025925 A1    3/2012

OTHER PUBLICATIONS

Yu, L., et al., "Identification and expression of novel isoforms of human stromal cell-derived factor 1," *Gene*, 2006, 374:174-179.
Sneddon, J., et al., "Stem Cell Therapies for Treating Diabetes: Progress and Remaining Challenges," *Cell Stem Cell*, 2018, 22: 810-818.
Ricordi, C., "Lilly Lecture 2002—Islet Transplantation: A Brave New World," *Diabetes*, 2003, 52: 1595-1603.
King, A., "The use of animal models in diabetes research," *British Journal of Pharmacology*, 2012, 166:877-894.
Perlman, R., "Mouse models of human disease: An evolutionary perspective," *Evol. Med. Public Health*, 2016, 2016(1): 170-176.
"Researchers find striking differences between human and animal insulin-producing islet cells," Diabetes Research Institute Foundation Press Release, Feb. 2006, available at: https://www.diabetesresearch.org/differences-between-human-and-animal-insulin-producing-islet-cells.

(Continued)

*Primary Examiner* — Michail A Belyavskyi
(74) *Attorney, Agent, or Firm* — Faegre Drinker Biddle & Reath LLP

(57) ABSTRACT

Described herein are human transgenic beta cells expressing fugetactic levels of CXCL12 to a subject in need thereof. Also described herein are beta cells comprising a transgene comprising a nucleic acid sequence encoding CXCL12.

3 Claims, 5 Drawing Sheets

Specification includes a Sequence Listing.

(56) References Cited

OTHER PUBLICATIONS

Chong, A., et al., "Lessons and Limits of Mouse Models," *Cold Spring Harb. Perspect. Med.,* 2013, 3(12): 1-16.

Aboumrad, E., et al., "The CXCR4/CXCL12 (SDF-1) signalling pathway protects non-obese diabetic mouse from autoimmune diabetes," *Clinical and Experimental Immunology,* 2007, 148(3): 432-439.

Pericin, M., et al., "Allogeneic β-islet cells correct diabetes and resist immune rejection," *PNAS,* 2002, 99(12): 8203-8206.

European Patent Office, International Search Report and Written Opinion for International Application No. PCT/US2018/053599, dated Nov. 28, 2018.

Vianello, F., et al., "Fugetaxis: active movement of leukocytes away from a chemokinetic agent," *J. Mol. Med.,* 2005, 83: 752-763.

Poznansky, M., et al., "Thymocyte emigration is mediated by active movement away from stroma-derived factors," *J. Clin. Invest.,* 2002, 109(8): 1101-1110.

Sremac, M., et al., "Preliminary Studies of the Impact of CXCL12 on the Foreign Body Reaction to Pancreatic Islets Microencapsulated in Alginate in Nonhuman Primates," *Transplantation Direct,* 2019, 5(5): e447.

Massachusetts General Hospital, "Protein that repels immune cells protects transplanted pancreatic islets from rejection: Transplanting islets encapsulated with CXCL12 restores blood sugar control without immunosuppression in animal models of diabetes," Feb. 18, 2015 [Press Release]. Retrieved from https://www.eurekalert.org/pub_releases/2015-02/mgh-ptr021115.php.

"Cloning Technique Used to Create Pancreatic Cells for Type 1 Diabetes." Diabetes Community, Support, Education, Recipes & Resources, Apr. 29, 2014 (4 pages), www.diabetes.co.uknews/2014/apr/cloning-technique-used-to-create-pancreatic-cells-for-type-1-diabetes-94233303.html.

Baek, K., et al., "Gene transfection for stem cell therapy," *Current Stem Cell Reports* 2(1): 52-61, 2016.

Cabrera, O., et al., "The unique cytoarchitecture of human pancreatic islets has implications for islet cell function," *Proceedings of the National Academy of Sciences* 103(7): 2334-2339, 2006.

Cermak, T., et al., "Efficient design and assembly of custom TALEN and other TAL effector-based constructs for DNA targeting," *Nucleic Acids Research* 39(12): e82, 2011 (11 pages).

Chira, S., et al., "Progresses towards safe and efficient gene therapy vectors," *Oncotarget* 6(31): 30675-30703, 2015.

Cong, L., et al., "Multiplex genome engineering using CRISPR/Cas systems," *Science* (2013): 819-823.

El-Haibi, C. P., et al., "CXCL13 mediates prostate cancer cell proliferation through JNK signalling and invasion through ERK activation," *Cell Proliferation* 44(4) (2011) (16 pages).

Gonzalez, F., et al., "An iCRISPR platform for rapid, multiplexable, and inducible genome editing in human pluripotent stem cells," *Cell Stem Cell* 15(2): 215-226, 2014.

Hardee, C. L., et al. "Advances in non-viral DNA vectors for gene therapy," *Genes* 8(65) (2017) (22 pages).

He, X., et al., "Knock-in of large reporter genes in human cells via CRISPR/Cas9-induced homology-dependent and independent DNA repair," *Nucleic Acids Research* 44(9) (2016): e85-e85.

Hockemeyer, D., et al., "Genetic engineering of human pluripotent cells using TALE nucleases," *Nature Biotechnology* 29(8): 731, 2011.

Hsu, P. D., et al., "Development and applications of CRISPR-Cas9 for genome engineering," *Cell* 157(6): 1262-1278, 2014.

Johannesson, B., et al., "Toward beta cell replacement for diabetes," *The EMBO Journal* 34(7): 841-855, 2015.

Joung, J. K., et al., "TALENs: a widely applicable technology for targeted genome editing," *Nature Reviews Molecular Cell Biology* 14(1): 49-55, 2013.

Kelly, O. G., et al., "Cell-surface markers for the isolation of pancreatic cell types derived from human embryonic stem cells," *Nature Biotechnology* 29(8) (2011) (9 pages).

Kroon, E., et al., "Pancreatic endoderm derived from human embryonic stem cells generates glucose-responsive insulin-secreting cells in vivo," *Nature Biotechnology* 26(4): 443-452, 2008.

Lowry, W. E., et al., "Generation of human induced pluripotent stem cells from dermal fibroblasts," *Proceedings of the National Academy of Sciences* 105(8): 2883-2888, 2008.

Maherali, N., et al., "Directly reprogrammed fibroblasts show global epigenetic remodeling and widespread tissue contribution," *Cell Stem Cell* 1(1): 55-70, 2007.

Mali, P., et al., "RNA-guided human genome engineering via Cas9," *Science* 339(6121): 823-826, 2013.

Mestas, J., et al., "Of mice and not men: differences between mouse and human immunology," *The Journal of Immunology,* 2004, 172(5): 2731-2738.

Miller, J. C., et al., "A Tale nuclease architecture for efficient genome editing," *Nature Biotechnology* 29(2): 143-150, 2010.

Millette, K., et al., "Gene Editing and Human Pluripotent Stem Cells: Tools for Advancing Diabetes Disease Modeling and Beta-Cell Development," *Current Diabetes Reports* 17(11): 116, 2017.

Millman, J. R., et al., "Generation of stem cell-derived β-cells from patients with type 1 diabetes," *Nature Communications* 7: 11463 (May 10, 2016) (9 pages).

Narayanavari, S. A., et al., "Sleeping Beauty transposon vectors for therapeutic applications: advances and challenges," *Cell and Gene Therapy Insights* 3(2) (2017) (28 pages).

Okita, K., et al., "Generation of germline-competent induced pluripotent stem cells," *Nature* 448(7151): 313-318, 2007.

Orlando, G., et al., "Cell replacement strategies aimed at reconstitution of the β-cell compartment in type 1 diabetes," *Diabetes* 63(5): 1433-1444, 2014.

Oumard, A., et al., "Recommended method for chromosome exploitation: RMCE-based cassette-exchange systems in animal cell biotechnology," *Cytotechnology* 50.1-3 (2006): 93-108.

Pagliuca, F. W., et al., "How to make a functional β-cell," *Development,* 2013, 140(12): 2472-2483.

Papeta, N., et al., "Long-term survival of transplanted allogeneic cells engineered to express a T cell chemorepellent," *Transplantation,* 2007, 83(2): 174-183.

Park, I., et al., "Reprogramming of human somatic cells to pluripotency with defined factors," *Nature* 451: 141-145, 2008.

Perl, S., et al., "Significant human β-cell turnover is limited to the first three decades of life as determined by in vivo thymidine analog incorporation and radiocarbon dating," *The Journal of Clinical Endocrinology & Metabolism* 95(10): E234-E239, 2010.

Petrova, N. V., et al., "Small molecule compounds that induce cellular senescence," *Aging Cell* 15(6): 999-1017, 2016.

Porteus, M. H., et al., "Gene targeting using zinc finger nucleases," *Nature Biotechnology* 23(8): 967-973, 2005.

Poznansky, M. C., et al., "Active movement of T cells away from a chemokine," *Nature Medicine* 6(5): 543-548, 2000.

Qadir, M. M. F., et al., "P2RY1/ALK3-Expressing Cells within the Adult Human Exocrine Pancreas Are BMP-7 Expandable and Exhibit Progenitor-like Characteristics," *Cell Reports* 22(9): 2408-2420, 2018.

Qi, M., "Transplantation of encapsulated pancreatic islets as a treatment for patients with type 1 diabetes mellitus," *Advances in Medicine,* vol. 2014 (2014) (15 pages).

Reyon, D., et al., "FLASH assembly of TALENs for high-throughput genome editing," *Nature Biotechnology* 30(5): 460-465, 2012.

Russ, H. A., et al., "Controlled induction of human pancreatic progenitors produces functional beta-like cells in vitro," *The EMBO Journal* 34(13): 1759-1772, 2015.

Sakata, N., et al., "Encapsulated islets transplantation: past, present and future," *World Journal of Gastrointestinal Pathophysiology,* 2012, 3(1): 19-26.

Schuetz, C., et al., "Islet cell transplantation: update on current clinical trials," *Current Transplantation Reports* 3(3): 254-263, 2016.

Shi, Y., et al., "Inducing embryonic stem cells to differentiate into pancreatic β cells by a novel three-step approach with activin A and all-trans retinoic acid," *Stem Cells* 23(5): 656-662, 2005.

(56) References Cited

OTHER PUBLICATIONS

Takahashi, K., et al., "Induction of pluripotent stem cells from mouse embryonic and adult fibroblast cultures by defined factors," *Cell* 126(4): 663-676, 2006.
Takahashi, K., et al., "Induction of pluripotent stem cells from adult human fibroblasts by defined factors," *Cell* 131(5): 861-872, 2007.
Tateishi, K., et al., "Generation of insulin-secreting islet-like clusters from human skin fibroblasts," *Journal of Biological Chemistry* 283(46): 31601-31607, 2008.
Tatum, J. A., et al., "Single-donor islet transplantation in type 1 diabetes: patient selection and special considerations," *Diabetes, Metabolic Syndrome and Obesity: Targets and Therapy* 10: 73-78, 2017.
Tipanee, J., et al., "Preclinical and clinical advances in transposon-based gene therapy," *Bioscience Reports* 37(6) (2017) (20 pages).
Urnov, F. D., et al., "Genome editing with engineered zinc finger nucleases," *Nature Reviews Genetics* 11 (9): 636-646, 2010.
Votey, M., et al., "Of Mice and Men: How the NPOD Program Is Changing the Way Researchers Study Type 1 Diabetes," *DiaTribe*, Aug. 21, 2015 (2 pages), diatribe.org/mice-and-men-how-npod-program-changing-way-researchers-study-type-1-diabetes.
Walsh, N. C., et al., "Humanized mouse models of clinical disease," *Annual Review of Pathology: Mechanisms of Disease* 12:187-215, 2017.
Wernig, M., et al., "In vitro reprogramming of fibroblasts into a pluripotent ES-cell-like state," *Nature* 448(7151): 318-325, 2007.
Yano, T., et al., "Stromal cell-derived factor-1 (SDF-1/CXCL12) attenuates diabetes in mice and promotes pancreatic beta-cell survival by activation of the prosurvival kinase Akt," *Diabetes*, 2007, 56(12): 2946-57.
Yu, J., et al., "Induced pluripotent stem cell lines derived from human somatic cells," *Science* 318: 1917-1920, 2007.
Zhang, Z., et al., "CRISPR/Cas9 genome-editing system in human stem cells: current status and future prospects," *Molecular Therapy-Nucleic Acids* 9: 230-241,2017.
Brehm, M. A., et al, "Advancing animal models of human type 1 diabetes by engraftment of functional human tissues in immunodeficient mice," *Cold Spring Harbor Perspectives in Medicine* 2(5): a007757, 2012.
Collier, J. J., et al., "Pro- and antiapoptotic proteins regulate apoptosis but do not protect against cytokine-mediated cytotoxicity in rat islets and β-cell lines," *Diabetes* 55(5): 1398-1406, 2006.
Goping, I. S., et al., "Cytotoxic T lymphocytes overcome Bcl-2 inhibition: target cells contribute to their own demise," *Blood* 111(4): 2142-2151, 2008.
Luther, S. A., et al., "Differing activities of homeostatic chemokines CCL19, CCL21, and CXCL12 in lymphocyte and dendritic cell recruitment and lymphoid neogenesis," *The Journal of Immunology* 169(1): 424-433, 2002.
Roep, B. O., et al., "Animal models have little to teach US about Type 1 diabetes: 1. In support of this proposal," *Diabetologia*, 2004, 47(10): 1650-1656.
Van Craenenbroeck, K., et al., "Episomal vectors for gene expression in mammalian cells," *European Journal of Biochemistry* 267(18): 5665-5678, 2000.
Helman, A., et al., "$p^{16Ink4a}$-induced senescence of pancreatic beta cells enhances insulin secretion," *Nature Medicine*, 2016, 22(4): 412-422.
Sundararaman, S., et al., "Plasmid-based transient human stromal cell-derived factor-1 gene transfer improves cardiac function in chronic heart failure," *Gene Therapy*, 2011,18: 867-873.
Penn, M.S., et al., "SDF-1 in myocardial repair," *Gene Therapy*, 2012, 19: 583-587.
Orimo, A., et al., "Stromal Fibroblasts Present in Invasive Human Breast Carcinomas Promote Tumor Growth and Angiogenesis through Elevated SDF-1/CXCL12 Secretion," *Cell*, 2005, 121: 335-348.
Ilhan, A., et al., "CXCL12/SDF-1 over-expression in human insulinomas and its biological relevance," *Molecular and Cellular Endocrinology*, 2009, 298:1-10.

GenBank E09668.1, cDNA encoding human SDF-1 alpha, 2005 (2 pages).
GenBank E09669.1, cDNA of human SDF-1 beta isoform, 2005 (2 pages).
Leach, C., "The Mouse Trap," *Insulin Nation*, Nov. 18, 2013, available at: https://insulinnation.com/treatment/cure-insight/the-mouse-trap/.
Yang, H., et al., "Human β Cells Are Exceedingly Resistant to Streptozotocin in Vivo," *Endocrinology*, 2002, 143(7): 2491-2495.
Bhatt, J.M., et al., "Expression of Epitope-Tagged Proteins in Mammalian Cells in Culture," *Methods Mol. Biol.*, 2016, 1474: 3-24 [Abstract].
Cerignoli, F., et al., "In vitro immunotherapy potency assays using real-time cell analysis," *PLOS One*, 2018, available at: https://doi.org/10.1371/journal.pone.0193498.
Herberts, C., et al., "Risk factors in the development of stem cell therapy," *J. Transl. Med.*, 2011, 9:29.
Stewart, D., "CRISPR-Cas9 DNA Editing Possibly Linked to Cancer, But CRISPR-Cas13d RNA Editing Could Offer New Avenues for Treatment," *Dark Daily*, Nov. 7, 2018, available at: https://www.darkdaily.com/crispr-cas9-dna-editing-possibly-linked-to-cancer-but-crispr-cas13d-rna-editing-could-offer-new-avenues-for-treatment/.
Zhong, Y., et al., "Targeting Interleukin-2-inducible T-cell Kinase (ITK) and Resting Lymphocyte Kinase (RLK) Using a Novel Covalent Inhibitor PRN694," *J. Biol. Chem.*, 2015, 290(10): 5960-5978.
Ansari, A., et al., "Cellular GFP Toxicity and Immunogenicity: Potential Confounders in in Vivo Cell Tracking Experiments," *Stem Cell Rev.*, 2016, 12(5): 553-559.
Kaja, S., et al., "Quantification of Lactate Dehydrogenase for Cell Viability Testing Using Cell Lines and Primary Cultured Astrocytes," *Current Protocols in Toxicology*, 2017, Suppl 72: 2.26.1-2.26.10.
The International Bureau of WIPO, International Preliminary Report on Patentability for International Application No. PCT/US2018/053599, dated Apr. 16, 2020.
Kiewlich Declaration signed Nov. 20, 2019, and submitted in U.S. Appl. No. 16/370,606.
Altieri, P., et al., "5-fluorouracil causes endothelial cell senescence: potential protective role of glucagon-like peptide 1," *British Journal of Pharmacology*, 2017, 174: 3713-3726.
Xiao, H., et al., "*Angelica sinensis* Polysaccharides Ameliorate Stress-Induced Premature Senescence of Hematopoietic Cell via Protecting Bone Marrow Stromal Cells from Oxidative Injuries Caused by 5-Fluorouracil," *Int. J. Mol. Sci.*, 2017, 18: 2265.
Copenhaver, M., et al., "Type 1 diabetes: where are we in 2017?," *Transl. Pediatr.*, 2017, 6(4): 359-364.
Teta, M., et al., "Very Slow Turnover of β-Cells in Aged Adult Mice," *Diabetes*, 2005, 54: 2557-2567.
Focaccetti, C., et al., "Effects of 5-Fluorouracil on Morphology, Cell Cycle, Proliferation, Apoptosis, Autophagy and ROS Production in Endothelial Cells and Cardiomyocytes," *PLoS ONE*, 2015, 10(2): eQ115686. doi: 10.1371/journal.pone.0115686.
Naparstek, Y., et al., "Effector T lymphocyte line cells migrate to the thymus and persist there," *Nature*, 1982, 300: 262-264. [Abstract only].
Route of administration, (n.d.). In *Wikipedia*. Retrieved Aug. 19, 2020, from https://en.wikipedia.org/wiki/Route_of_administration.
United States Patent and Trademark Office, Notice of Allowance in U.S. Appl. No. 16/370,606 dated Apr. 20, 2020.
Charles, M. A., et al., "Immune islet killing mechanisms associated with insulin-dependent diabetes: in vitro expression of cellular and antibody-mediated islet cell cytotoxicity in humans," *J. Immunol.*, 1983, 130(3): 1189-1194.
Olivier, V., et al., "Comparative particle-induced cytotoxicity toward macrophages and fibroblasts," *Cell Biology and Toxicology*, 2003, 19: 145-159.
Altenburg, J., et al., "A Naturally Occurring Splice Variant of CXCL12/Stromal Cell-Derived Factor 1 Is a Potent Human Immunodeficiency Virus Type 1 Inhibitor with Weak Chemotaxis and Cell Survival Activities," *J. Virol.*, 2007, 81(15): 8140-8148.
Rabinovitch, A., et al., "Transfection of Human Pancreatic Islets With an Anti-Apoptotic Gene (bcl-2) Protects β-Cells From Cytokine-Induced Destruction," *Diabetes*, 1999, 48(6): 1223-1229.

(56) References Cited

OTHER PUBLICATIONS

Götherström, C., et al., "Fetal and adult multipotent mesenchymal stromal cells are killed by different pathways," *Cytotherapy,* 2011, 13(3): 269-278.
Berezhnoi, A. E., et al., "High-dose Gamma-Irradiation Enhance Expression of Transgene Under Control of Immediate-Early CMV Promoter in Stably Transfected Tumor Cells," *Mol. Biol. (Mosk)*, 2008, 42(3): 501-509. [Abstract only].
Liang, X., et al., "Human bone marrow mesenchymal stem cells expressing SDF-1 promote hematopoietic stem cell function of human mobilised peripheral blood CD34+ cells in vivo and in vitro," *Int. J. Radiat. Biol.,* 2010, 86(3): 230-237. [Abstract only].
Zhang, L., et al., "CXCL12 overexpression promotes the angiogenesis potential of periodontal ligament stem cells," *Sci. Rep.,* 2017, 7: 10286.
Final Office Action dated Jun. 29, 2020 in U.S. Appl. No. 16/146,980.
Appeal Brief filed Nov. 20, 2020 in U.S. Appl. No. 16/146,980.
Kiewlich Declaration signed Feb. 7, 2020, and submitted in U.S. Appl. No. 16/146,980.
Examiner's Answer mailed Dec. 28, 2020 in in U.S. Appl. No. 16/146,980.
Reply Brief filed Feb. 24, 2021 in U.S. Appl. No. 16/146,980.

GENETICALLY MODIFIED STEM CELLS

CROSS-REFERENCE TO RELATED APPLICATIONS

This application is a continuation of U.S. application Ser. No. 16/826,104, filed Mar. 20, 2020, now U.S. Pat. No. 10,982,190, which is a continuation of U.S. application Ser. No. 16/370,606, filed Mar. 29, 2019, now U.S. Pat. No. 10,696,950, which is a continuation of U.S. application Ser. No. 16/146,980, filed Sep. 28, 2018 now abandoned, which claims priority to U.S. Provisional Application Nos. 62/567,604, filed Oct. 3, 2017; 62/568,117, filed Oct. 4, 2017; 62/637,913, filed Mar. 2, 2018; 62/662,651, filed Apr. 25, 2018; 62/694,634, filed Jul. 6, 2018; 62/696,603, filed Jul. 11, 2018; 62/717,587, filed Aug. 10, 2018; 62/719,975, filed Aug. 20, 2018; and 62/734,910, filed Sep. 21, 2018; each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Apr. 5, 2021, is named 220710-0001-04-SL.txt and is 8,958 bytes in size.

FIELD OF THE INVENTION

The invention is directed to genetically modified, human beta cells as well as methods using such cells. The genetically modified (transgenic), human beta cells express a fugetactic amount of a fugetactic agent thereby imparting protection against human mononuclear immune cells. In one embodiment, the fugetactic agent is, for example, CXCL12 or CXCL13. In one embodiment, the transgenic beta cells comprise a vector, wherein the vector comprises a nucleic acid sequence encoding a fugetactic agent and preferably a human fugetactic agent. In one embodiment, the transgenic beta cells are further modified to be senescent. Methods of this invention include use these cells to express insulin in a hyperglycemic environment including those found in diabetic patients, in particular type I diabetic patients.

BACKGROUND OF THE INVENTION

Beta cells are responsible for producing insulin in the pancreas. In subjects with type 1 diabetes (T1D), beta cells are attacked and destroyed by the immune system and, as a result, subjects with T1D cannot efficiently produce their own insulin. *Cloning technique used to create pancreatic cells for type 1 diabetes*, Diabetes.Co.Uk, www.diabetes.co.uk/news/2014/apr/cloning-technique-used-to-create-pancreatic-cells-for-type-1-diabetes-94233303.html (Apr. 29, 2014).

Type 2 diabetes (T2D) occurs when a subject's persistently high blood sugar overwhelms the capacity of a subject's beta-cells to produce enough insulin to prevent hyperglycemia in the subject and leads to beta-cell malfunction, de-differentiation, and death. Felicia W Pagliuca & Douglas A. Melton, How to make a functional β-cell," *Development* 2013, 140(12), 2472-2483.

Allogeneic beta cell transplantation, also known as islet cell transplantation, from a normal donor to a diabetic recipient has been considered as a method of treating diabetes. However, infiltration of mononuclear immune cells (T-cells, B-cells, and NK cells) results in the failure of the beta cell transplantation. *Cloning technique used to create pancreatic cells for type 1 diabetes*, Diabetes.Co.Uk, www.diabetes.co.uk/news/2014/apr/cloning-technique-used-to-create-pancreatic-cells-for-type-1-diabetes-94233303.html (Apr. 29, 2014); Alan H. Cruickshank & Emyr W Benbow, "Recurrence of Diabetes," Pathology of the Pancreas (2d ed. 1995); Felicia W Pagliuca & Douglas A. Melton, "How to make a functional β-cell," *Development* 2013, 140(12), 2472-2483.

Current clinical practice is to transplant islets containing beta cells into the liver via the portal vein, with the rationale that the majority of insulin released from the pancreas is utilized in the liver and the site is easily accessible by a minimally invasive procedure. However, half of the beta cells die shortly after transplantation, and this is thought to be due to low oxygen tension, an active immune response, and high levels of toxins and drugs in the liver. In addition, the instant blood mediated inflammatory reaction (IBMIR) encapsulates transplanted islets in a fibrin clot and enhances the immune reaction against the graft. Therefore, several alternative sites for transplantation have been tested including the intestine, kidney capsule, omentum, and subcutaneous, which may be best for patient safety, but have not been fully evaluated for systemic release of insulin.

To prevent their exposure to mononuclear immune cells, beta cells have been encapsulated in devices that have been reported to serve a dual function of isolating these cells from immune destruction and protecting the host from the graft. Immune protection is required when non-autologous cells (e.g., allogeneic or xenogeneic cells) are used for transplantation, or if autologous cells are transplanted into an autoimmune environment, such as a Type 1 diabetic patient. This can be achieved by blocking the cellular response via physical isolation of the cells using semi-permeable membranes or scaffolds. This approach reduces the need for immunosuppression and has recently been reviewed in detail elsewhere (Sakata et al, World J Gastrointest Pathophysiol. 2012; 3:19-26; Qi, Adv Med. 2014; 2014:429710). Encapsulation also prevents cells from escaping the location of the graft, and allows for removal, if needed. This is particularly relevant, as uncontrolled differentiation and growth, e.g. teratomas, have often been observed in mice grafted with stem cell-derived pancreatic precursors (Kroon et al, Nat Biotechnol. 2008; 26:443-452; Kelly el al, Nat Biotechnol. 2011; 29:750-756.). Teratoma formation may be preventable by generating grafts consisting of a pure population of mature beta cells, either by using cell purification (Kelly et al, 2011) or by improving differentiation methods. Encapsulation also prevents potential metastasis if insulinomas/teratomas are formed by the transplanted cells.

This approach requires efficient and reproducible micro-encapsulation protocols, and some cells may die within the encapsulated material without the possibility of being cleared or removed. Some reports have shown micro-encapsulated beta cells can remain viable up to 6 months after implantation (Orlando et al, Diabetes. 2014; 63:1433-1444). This means that repeated surgeries are required to replace the micro-encapsulation devices when the device is no longer functional.

In view of the above, there is a long unmet need to develop technology that effectively treats diabetes and, in particular, type 1 diabetes.

SUMMARY OF THE INVENTION

This invention is directed to transgenic, human beta cells as well as transgenic, senescent, human beta cells that express an effective amount of a fugetactic agent so as to render these cells resistant to human immune cells. Fugetactic agents are well known in the art including "CXCL12". This cytokine, also known as SDF-1, is produced by thymic and bone marrow stroma (see e.g. U.S. Pat. No. 5,756,084, entitled: "Human stromal derived factor 1α and 1β.," issued May 26, 1998, to Honjo, et al.). CXCL12 has been reported to repel effector T-cells while recruiting immune-suppressive regulatory T-cells to an anatomic site. See, e.g., Poznansky et al., Nature Medicine 2000, 6:543-8. CXCL12 and its receptor CXCR4 are also reported to be an integral part of angiogenesis.

Agents other than CXCL12 are also disclosed to repel immune cells, including, without limitation, gp120, other CXCR4 ligands, IL-8, CXCR4-binding antibodies, CXCL13, CXCR5 ligands, CXCR5-binding antibodies, and the like.

An embodiment of the invention is a transgenic human beta cell expressing an effective amount of a fugetactic agent, preferably CXCL12 or CXCL13, so as to render the cell resistant to human immune cells. In one embodiment, such fugetactic effective amounts of the fugetactic agent are generated by introduction of a human transgene for the agent (e.g., CXCL12, CXCL13) into the beta cell or a precursor of the beta cell (e.g., a pluripotent stem cell). These human transgenic beta cells are further characterized as expressing insulin in a hyperglycemic environment. As such, these cells can be used in a method for treating diabetes in a subject. The transgenic human beta cells used in the methods described herein may be autologous or non-autologous, e.g., allogenic, beta cells. In one embodiment, the patient suffers from T1D. In another embodiment, the transgenic human beta cell can be modified to be senescent (incapable of division) such that any further differentiation of these cells into cancer cells is eliminated and apoptotic induction arising due to inappropriate cell division is negated.

An embodiment of this invention uses beta cells, e.g., autologous or allogenic beta cells, either obtained or derived from a non-diabetic human subject or a human subject suffering from diabetes. These beta cells include a functional fugetactic agent (e.g., CXCL12, CXCL13) expression vector. Such a vector is designed to express the agent in the transgenic beta cells at a level sufficient to generate a fugetactic buffer around the beta cells. Without wishing to be bound by theory it is contemplated that this buffer allows the beta cells to resist immune cell attack, but still express insulin as would be necessary to maintain proper blood sugar levels in a diabetic subject. The generation of autologous beta cells from patients suffering from diabetes is known in the art. See, for example, Egli, et al., EMBO J. 2015 Apr. 1; 34(7): 841-855, which is incorporated herein by reference in its entirety. Allogeneic beta cells derived from stem cells are commercially available.

An aspect of this invention is the administration of transgenic human beta-cells comprising a transgene encoding a fugetactic agent (e.g., CXCL12, CXCL13) to subjects in need thereof to modulate the levels of insulin and to treat diabetes in the subject. In addition, the expression of a sufficient amount of a fugetactic agent protects against the risk of destruction of the transgenic beta cells by mononuclear immune cell infiltration. The transgenic human beta cells may be autologous or allogeneic. In an embodiment of this invention, the transgenic beta cells are autologous beta cells derived from the patient suffering from diabetes. In another embodiment, the transgenic beta cells are allogeneic human beta cells. In another embodiment, the patient is suffering from type 1 diabetes.

Another aspect of this invention relates to transgenic human beta cells that are capable of expressing a fugetactic effective amount of a fugetactic agent (e.g., CXCL12, CXCL13) so as to be resistant to immune destruction. The fugetactic agent (e.g., CXCL12, CXCL13) may be an endogenous agent, i.e., an agent expressed by the subject to be treated, or an exogenous agent, e.g., an agent from a non-autologous source or a modified fugetactic agent. In one embodiment, the gene encoding the fugetactic agent in the beta cells is modified to be over-expressed compared to the unmodified gene. Methods for modifying gene expression are known in the art, for example, site-directed gene editing to replace the endogenous promoter with a different promoter (e.g., a constitutive promoter, an inducible promoter, etc.). In one embodiment, a recombinant polynucleotide encoding the fugetactic agent is inserted into the beta cells, such that the fugetactic agent is expressed from the recombinant polynucleotide. Methods for inserting recombinant genes into a cell (transduction, transfection, etc.) are well known in the art, as are methods for making vectors with recombinant polynucleotides for insertion in to cells.

In some embodiments, the fugetactic agent is a modified fugetactic agent. For example, the polypeptide sequence of the fugetactic agent may be modified to increase circulating half-life, to incorporate conservative amino acid changes, enhance binding to an extracellular matrix, improve activity of the agent, etc. Accordingly, genes encoding a modified fugetactic agent (e.g., CXCL12 or CXCL13) can be modified such the gene has at least 95% sequence identity to the native gene and preferably 99% sequence identity to the native gene. Likewise, the amino acid sequence of the modified fugetactic agent (e.g., modified CXCL12 or CXCL13) has a sequence identity to the native agent of at least 95% and preferably 99%.

In one embodiment, there is provided a human beta cell comprising a vector that itself comprises a nucleic acid sequence encoding human CXCL12 or modified CXCL12 wherein said beta cell is made resistant to human immune cells.

In one embodiment, the human transgenic beta cell is an autologous beta cell obtained from a subject with type 1 diabetes.

In one embodiment, the human beta cell is an allogenic beta cell.

In one embodiment, the human mononuclear immune cells comprise NK cells, T cells and B cells. In one embodiment, the T cells comprise cytotoxic T cells.

In one embodiment, the transgenic human beta cell expresses human CXCL12 at a fugetactic amount.

In one embodiment, the human CXCL12 is selected from the group consisting of CXCL12 alpha and CXCL12 beta.

In one embodiment, the human transgenic beta cell comprises a transgenic regulatory region upstream of an endogenous CXCL12 coding region wherein said beta cell is resistant to human immune cells. Preferably, the endogenous CXCL12 coding region regulatory region comprises a constitutive promoter. In some embodiments, the endogenous CXCL12 coding region regulatory region comprises an inducible promoter.

In one embodiment, the human transgenic beta cell comprising a transgenic regulatory region upstream of an endogenous CXCL12 coding region wherein said beta cell is resistant to human immune cells is an autologous beta cell and, preferably, one obtained from a patient with diabetes.

In one embodiment, the human transgenic beta cell comprising a transgenic regulatory region upstream of an endogenous CXCL12 coding region wherein said beta cell is resistant to human immune cells is an allogenic beta cell.

In one embodiment, there is provided a human transgenic beta cell that comprises an expressible human CXCL12 or CXCL13 gene wherein said cell expresses a fugetactic effective amount of CXCL12 or CXCl13 so as to be resistant to human immune cells.

In one embodiment, the human, transgenic beta comprises the human gene for CXCL12.

In one embodiment, the human, transgenic beta cell comprise the human gene selected from the group consisting of CXCL12 alpha and CXCL12 beta.

In one embodiment, the human, transgenic beta cell comprises the human gene for CXCL12 beta.

In one embodiment, there is provided a human, transgenic, senescent beta cell that comprises an expressible human CXCL12 or CXCL13 gene wherein said cell expresses a fugetactic effective amount of CXCL12 or CXCL13 so as to be resistant to human immune cells and further wherein said cell is senescent.

In one embodiment, the human, transgenic, senescent beta cell comprises an expressible human gene for CXCL12 and which is capable of insulin expression in the presence of a hyperglycemic medium.

In one embodiment, the human, transgenic, senescent, beta cell comprises an expressible human gene selected from the group consisting of CXCL12 alpha and CXCL12 beta.

In one embodiment, the human, transgenic, beta cell comprises an expressible human gene is CXCL12 beta.

In one embodiment, there is provided a method for producing insulin in response to a hyperglycemic environment which method comprises contacting said environment with a population of human transgenic beta cells as described above.

In one embodiment, the human transgenic beta cells are resistant to human immune cells selected from the group consisting of T cells, B cells, NK cells, and mixtures thereof.

In one embodiment, the beta cells described herein are obtained by:
(a) obtaining a population of human progenitor cells or human pluripotent stem cells from a human subject;
(b) differentiating the subject's progenitor cells or pluripotent stem cells into beta cells; and
(c) introducing a nucleic acid molecule encoding the fugetactic agent into the beta cells.

In one embodiment, the fugetactic agent is a cytokine, a chemokine, a CXCR4-binding antibody, a CXCR4 ligand, a CXCR5-binding antibody, or a CXCR5 ligand.

In one embodiment, the fugetactic agent is CXCL12, CXCL13, gp120, or IL-8.

In one aspect is provided a method for promoting survival of beta cells in a biological sample comprising immune cells by modifying beta cells to express a fugetactic agent at a level sufficient to inhibit or block immune cells from killing said beta cell.

DETAILED DESCRIPTION OF THE INVENTION

Figure 1:
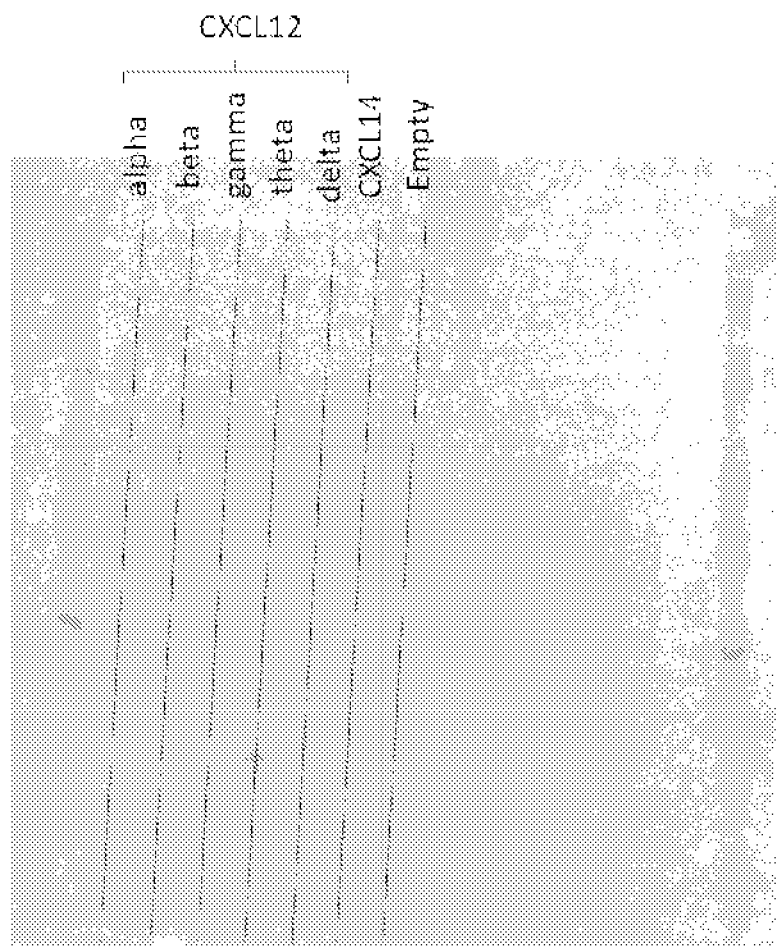
FIG. 1 is a photograph of a Western blot, showing relative amounts of CXCL12alpha, CXCL12beta, CXCL12gamma, CXCL12theta, and CXCL12delta, and CXCL14, when each is overexpressed in beta cells.

This invention provides for autologous/allogeneic human beta cells that are transgenic and comprise a transgene encoding a human fugetactic agent (e.g., CXCL12, CXCL13) or have been genetically modified to express or overexpress an endogenous (human) fugetactic agent (e.g., CXCL12, CXCL13) in fugetactic amounts. In a preferred embodiment, the transgenic beta cells described herein are further modified to be senescent. In another of its method aspects, the beta cells are modified or treated so as to express an effective amount of a fugetactic agent (e.g., CXCL12, CXCL13) so as to inhibit immune destruction of the transgenic human beta cells and to produce insulin in response to a hyperglycemic environment.

Prior to disclosing this invention in further detail, the following terms will first be defined. If a term is not defined, it has its generally accepted scientific meaning as understood in the art.

The term "CXCL13" refers to all known isoforms thereof. As CXCL13 is known to mediate certain cancer cell proliferation, it is not preferred. See, e.g., www.ncbi.nlm.nih.gov/pmc/articles/PMC3839818/

The term "fugetaxis" or "fugetactic" refers to the ability of an agent to repel (or chemorepel) an eukaryotic cell with migratory capacity. A fugetactic amount of CXCL12 or CXCL13 (or other fugetactic agent) expressed by a cell is an amount sufficient to block or inhibit immune cell migration towards the cell or in some aspects repel the immune cells from the cell.

The term "human immune cell" is used interchangeably with the term "human mononuclear immune cells" and includes NK cells, T cells, and B cells.

The term "immune cell-resistant" or "stealth to the immune system" indicates that the beta cell expresses an amount of fugetatic agent that is sufficient to block or inhibit immune cell migration towards the cell or in some aspects repel the immune cells from the beta cell. In a preferred embodiment, such blockage or inhibition is measured by the extent of cell death after exposure of the beta cells of this invention to human mononuclear immune cells (e.g., PBMCs). Cell death can be assessed by release of lactate dehydrogenase (LDH) from cells that have undergone lysis. Preferably, immune cell resistant beta cells of this invention can be assessed by cells that evidence less than 50% of the LDH levels relative to control at a ratio of about 30:1 immune cells to beta cells of this invention over a two day period of incubation. More preferably, the immune resistant beta cells evidence less than 60% of the LDH level relative to control; and even more preferably, less than 75% of the LDH level relative to control; and most preferably, less than 95% of the LDH level relative to control. The procedure for assessing LDH levels is set forth in example 2 herein.

A fugetactic agent is an agent that has fugetactic activity. Fugetactic agents may include, without limitation, CXCL12, CXCL13, gp120, IL-8, CXCR4-binding antibodies, CXCR4 ligands, CXCR5-binding antibodies, or CXCR5 ligands.

The term "effector T-cell" refers to a differentiated T-cell capable of mounting a specific immune response by releasing cytokines.

The term "regulatory T-cell" refers to a T-cell that reduces or suppresses the immune response of B-cells or of other T-cells to an antigen.

The terms "CXCL12" or "SDF-1 polypeptide" refer to cytokines well-known in the art (see, for example, Table 1). In an embodiment, the terms refer to a protein or fragment thereof that binds a CXCL12 specific antibody and that has chemotaxis or fugetaxis activity. Chemotaxis or fugetaxis activity is determined by assaying the direction of T cell migration (e.g., toward or away from an agent of interest). See, e.g., Poznansky et al., Nature Medicine 2000, 6:543-8; N. Papeta et al., "Long-term survival of transplanted allogeneic cells engineered to express a T Cell chemorepellent," *Transplantation* 2007, 83(2), 174-183. "Fugetaxis" or "Fugetactic migration" is the movement of a migratory cell away from an agent source (i.e., towards a lower concentration of agent). It is understood that the term "CXCL12" refers to all known isoforms thereof including the alpha, beta, gamma, delta, epsilon, phi and theta isoforms. Preferred CXCL12 isoforms are the alpha and beta. CXCL12 is known to induce angiogenesis.

The terms "type 1 diabetes" and "type 2 diabetes" refer to two major pathophysiologies related to increased glycemia. Type 1 diabetes is characterized by autoimmune attack against the pancreatic insulin-producing beta-cells whilst type 2 diabetes is associated with poor beta-cell function and increased peripheral insulin resistance. Similar to Type 1, beta-cell death is also observed in Type 2 diabetes. Type 1 and often Type 2 diabetes requires the person to inject insulin. Type 1 diabetes is typically characterized by loss of the insulin-producing beta-cells of the islets of Langerhans in the pancreas leading to insulin deficiency. This type of diabetes can be further classified as immune-mediated or idiopathic. The majority of Type 1 diabetes is of the immune-mediated nature, where beta-cell loss is due to a T-cell mediated autoimmune attack. Type 2 diabetes is characterized by beta-cell dysfunction in combination with insulin resistance. The defective responsiveness of body tissues to insulin is believed to involve the insulin receptor and downstream cellular signaling. Similar to Type 1 diabetes an insufficient beta cell mass is also a pathogenic factor in many Type 2 diabetic patients. In the early stage of Type 2 diabetes, hyperglycemia can be reversed by a variety of measures and medications that improve insulin secretion and reduce glucose production by the liver. As the disease progresses, the impairment of insulin secretion occurs, and therapeutic replacement of insulin may sometimes become necessary in certain patients.

A "subject" or "patient" refers to a mammal, preferably to a human subject.

A "subject in need thereof" or "patient in need thereof" is a subject having Type 1 or Type 2 diabetes.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

In this disclosure, "comprises," "comprising," "containing" and "having" and the like can have the meaning ascribed to them in U.S. Patent law and can mean "includes," "including," and the like: "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "about" when used before a numerical designation, e.g., temperature, time, amount, concentration, and such other, including a range, indicates approximations which may vary by (+) or (−) 10%, 5%, 1%, or any subrange or subvalue there between. Other definitions appear in context throughout this disclosure.

An aspect of this invention are transgenic beta cells, e.g., human autologous beta cells or non-autologous beta cells, e.g., allogeneic beta cells, comprising a nucleic acid encoding a fugetactic agent (e.g., CXCL12, CXCL13) in operable linkage with a promoter, such that the fugetactic agent (e.g., CXCL12, CXCL13) is expressed at a fugetactic level in the beta cell microenvironment. The promoter may be a promoter endogenous to the beta cell or heterologous to, but functional, in the beta cell. Preferably, the nucleic acid encoding the fugetactic agent (e.g., CXCL12, CXCL13) is endogenous to the subject being treated with the transgenic beta cells. In one embodiment, the allogeneic beta cell is derived from a non-T1D donor.

An aspect of this invention are human beta cells comprising a genetically modified endogenous human gene encoding a fugetactic agent (e.g., CXCL12, CXCL13) wherein the gene is modified to comprise a heterologous promoter in operable linkage with the fugetactic agent-encoding sequence, such that the fugetactic agent is expressed from the endogenous gene at a fugetactic level in the beta cell microenvironment. The promoter may be introduced into the beta cells to be in operable linkage with the fugetactic agent-encoding sequence using genome editing techniques known in the art. It is well known that CXCL12 has several isoforms including the alpha, beta, gamma, and theta. In a preferred embodiment, the isoform employed is CXCL12 beta. The transgenic human beta cells described herein produce insulin in response to a hyperglycemic environment. The term "insulin" is meant to cover both pro-insulin and insulin.

In general, this invention provides for beta cells, and preferably human beta cells, that express a fugetactic agent (e.g., CXCL12, CXCL13) at a level sufficient to block or inhibit migration of immune cells (e.g., human immune cells) to the beta cells or sufficient to repel immune cells. The terms immune cells and mononuclear cells (T-cells, B-cells, and NK cells) may be used interchangeably. The ability of a fugetactic agent (e.g., CXCL12, CXCL13) polypeptide to repel immune cells (e.g., effector T-cells) can be assessed in vitro, using a boyden chamber assay. See, e.g., as previously described in Poznansky et al., Journal of Clinical Investigation, 109, 1101 (2002). Alternatively, the viability of transgenic human beta cells is assessed by combining such cells with human PBMC. The rate of cell death can be evaluated by measuring one or more cell death markers over time. One such marker commonly used is lactate dehydrogenase (LDH) that is released during cell necrosis.

Without wishing to be bound by any theory, Applicant contemplates that in an aspect of this invention the amount of fugetactic agent (e.g., CXCL12, CXCL13) produced by the transgenic beta cell is sufficient to provide a fugetactic effect in the beta-cell microenvironment, but is not produced in an amount sufficient to raise the systemic levels of the agent and upset the balance between the beneficial effects of the agent in one process while producing deleterious consequences in another. In addition, CXCL12 is known to induce angiogenesis when bound to its receptor CXCR4. Again, without being bound by any theory, it is contemplated that the microenvironment of the implanted transgenic beta cells expressing CXCL12 will induce an angiogenic response that enhance the survivability of the implanted cells.

The fugetactic effective amount of a fugetactic agent (e.g., CXCL12, CXCL13) is any amount sufficient to block immune cell from killing the transgenic beta cells. For example a fugetactic effective amount of fugetactic agent (e.g., CXCL12, CXCL13) in the transgenic beta cell microenvironment may be at least about 100 ng/mL, and preferably at least 100 nM. In some embodiments, the amount of fugetactic agent (e.g., CXCL12, CXCL13) in the transgenic beta cell microenvironment is at least about 1000 ng/mL. For example, the following specific ranges that are suitable for this invention: from about 100 nM to about 200 nM, from about 100 nM to about 300 nM, from about 100 nM to about 400 nM, from about 100 nM to about 500 nM, from about 100 nM to about 600 nM, from about 100 nM to about 700 nM, from about 100 nM to about 800 nM, from about 100 nM to about 900 nM, or from about 100 nM to about 1 µM.

In embodiments, the fugetactic effective amount of fugetactic agent (e.g., CXCL12, CXCL13) in the transgenic beta cell microenvironment ranges from 20 ng/mL to about 5 µg/mL. In embodiments, the fugetactic effective amount ranges from 20 ng/mL to about 1 µg/mL. In embodiments, the amount of the fugetactic agent (e.g., CXCL12, CXCL13) in the beta cell microenvironment is a fugetactic sufficient amount that ranges from about 100 ng/mL to about 500 ng/mL, from about 500 ng/mL to 5 µg/mL, about 800 ng/mL to about 5 µg/mL, or from about 1000 ng/mL to about 5000 ng/mL. Without wishing to be bound by theory, it is contemplated that when transgenic and non-transgenic beta cells are used together, the transgenic beta cells can express sufficient amounts of the fugetactic agent such that the microenvironment creating the fugetactic effect extends to adjacent to non-transgenic beta cells. The fugetactic effective amount of fugetactic agent (e.g., CXCL12, CXCL13) in the transgenic beta cell microenvironment may be any value or subrange within the recited ranges, including endpoints.

Although mice and mouse DNA are widely used by immunologists to gain insight into the workings of the human immune system, there are significant differences between humans and mice. Accordingly, the fugetactic agent (e.g., CXCL12, CXCL13) encoded by the vector is preferably a human agent. Javier Mestas & Christopher C. W. Hughes, "Of Mice and Not Men: Differences between Mouse and Human Immunology," *Journal of Immunology* 2004, 172(5), 2731-2738; O. Cabrera et al., "The unique cytoarchitecture of human pancreatic islets has implications for islet cell function," *PNAS* 2006, 103(7), 2334-2339; M. Votey, "Of mice and men: how the nPOD program is changing the way researchers study type 1 diabetes," diaTribe, Network for Pancreatic Organ Donors with Diabetes (Aug. 21, 2015).

CXCL12 polypeptides are known in the art. See, e.g., Poznansky et al., Nature Medicine 2000, 6:543-8 and US Patent Publ. No. 20170246250 both of which are incorporated herein by reference in their entirety. The terms CXCL12 and SDF-1 may be used interchangeably. Exemplary CXCL12/SDF1 Isoforms are provided in Table I of US Publ. 20170246250. Exemplary CXCL12/SDF1 Isoforms are also provided in Table 1 (below):

TABLE 1

HUMAN CXCL12/SDF1 ISOFORMS

| Name | Accession Number | Accession Number Versions | Sequence |
|---|---|---|---|
| SDF-1 Alpha | NP_954637 | NP_954637.1 GI:40316924 | MNAKVVVVLV LVLTALCLSD GICPVSLSYRC PCRFFESHVA RANVKIILKIL NTPNCALQIV ARLKNNNRQV CIDPKIKWIQ EYLEKALNK (SEQ ID NO: 1) |
| SDF-1 Beta | P48061 | P48061.1 GI:1352728 | MNAKVVVVLV LVLTALCLSD GKPVSLSYRC PCRFFESHVA RANVKHLKIL INTPNCALQIV ARLKNNNRQV CIDPKLKWIQ EYLEKALNKR FKM (SEQ ID NO: 2) |
| SDF-1 Gamma | NP_001029058 | NP_001029058.1 GI:76563933 | MNAKVVVVLV LVLTALCLSD GKPVSLSYRC PCRFFESEIVA RANVKHLKIL NTPNCALQIV ARLKNNNRQV CIDPKLKWIQ EYLEKALNKG RREEKVGKKE KIGKKKRQKK RKAAQKRKN (SEQ ID NO: 3) |
| SDF-1 Delta | | Yu et al. Identification and expression of novel isoforms of human stromal cell-detived factor 1. Gene (2006) vol. 374 pp. 174-9 | MNAKVVVVIN LVLTALCLSD GKPVSLSYRC PCRFFESHVA RANVICHLKIL NTPNCALQIV ARLKNNNRQV GIDPKIKWIQ EYLEKALNNL ISAAPAGKRV IAGARALEIPS PPRACPTARA LCEIRMPPP EWSWPSPGDV (SEQ ID NO: 4) |

TABLE 1 -continued

HUMAN CXCL12/SDF1 ISOFORMS

| Name | Accession Number | Accession Number Versions | Sequence |
|---|---|---|---|
| SDF-1 Epsilon | | Yu et al. Identification and expression of novel isoforms of human stromal cell-derived factor 1. Gene (2006) vol. 374 pp. 174-9 | MNAKVVVVIN LVLTALCLSD GKIPVSLSYRC PCRFFESHVA RANYKEILKIL NTPNCALQIC ARLKNNNRQV CIDPKLKWIQ EYLEKALNNC (SEQ ID NO: 5) |
| SDF-1 Phi | | Yu et al. Identification and expression of novel isoforms of human strornal cell-derived factor I. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNKI WLYGNAETSR (SEQ ID NO: 6) |

In one embodiment, a CXCL12 polypeptide has at least about 85%, 90%, 92%, 95%, 96%, 97%, 98%, 99%, or 100% amino acid sequence identity to NP 001029058 and has chemokine or fugetactic activity. In one embodiment, a CXCL12 polypeptide has at least about 85%, 90%, 92%, 95%, 96%, 97%, 98%, 99%, or 100% amino acid sequence identity to SEQ ID NO: 1, SEQ ID NO: 2, SEQ ID NO: 3, SEQ ID NO: 4, SEQ ID NO: 5, or SEQ ID NO: 6, and has chemokine or fugetactic activity. Such sequence identity is based on the replacement of a first amino acid with a known conservative second amino acid. Such conservative replacements are well established in the art and the testing of the resulting modified CXCL12 polypeptide for its fugetactic properties are well known in the art. See, for example, Poznansky, supra.

CXCL13 peptides are known in the art. CXCL13 is also known as B lymphocyte chemoattractant (BLC) or B cell-attracting chemokine 1 (BCA-1), and these terms can be used interchangeably. For example, human CXCL13 can be found at Accession number Q53X90. In one embodiment, a CXCL13 polypeptide has an amino acid sequence comprising MKFISTSLLLMLLVSSLSPVQGVLEVYYTSLR-CRCVQESSVFIPRRFIDRIQILPRGNGCP RKEIIVWK-KNKSIVCVDPQAEWIQRMMEVLRKRSSSTLPVPVF-KRKIP (SEQ ID NO: 7). In one embodiment, a CXCL13 polypeptide has at least about 85%, 90%, 92%, 95%, 96%, 97%, 98%, 99/a, or 100% amino acid sequence identity to Q53X90 and has chemokine or fugetaxis activity. In one embodiment, a CXCL13 polypeptide has at least about 85%, 90%, 92%, 95%, 96%, 97%, 98%, 99%, or 100% amino acid sequence identity to SEQ ID NO: 7 and has chemokine or fugetaxis activity.

The transgenic beta cells used in the methods described herein may be autologous or non-autologous, e.g., allogenic beta cells. "Autologous" cells are cells from the same individual. "Allogeneic" cells are cells from a genetically similar but not identical a donor of the same species. Allogenic cells useful in the methods of this invention are preferably from a human subject. Allogenic cells useful in the methods of this invention maybe from a relative e.g., a sibling, a cousin, a parent, or a child, or a non-relative. Criteria for selecting an allogenic donor are well known in the art see, e.g., Tatum et al., Diabetes Metab Syndr Obes 2017: 10 73-78. Human allogeneic beta cells are commercially available and autologous beta cells are produced by the methods described by Egli, el al., supra.

In an embodiment, the transgenic human beta cells used in the methods of this invention are autologous transgenic beta cells that can be prepared by deriving beta cells from multipotent progenitor cells or pluripotent stem cells obtained from the patient by methods known in the art. These derived beta cells may comprise (e.g., be transfected, infected, etc. with) an expression vector comprising a nucleic acid sequence encoding the fugetactic agent (e.g., CXCL12, CXCL13).

Alternatively, the transgenic beta cells used in the methods of this invention may be prepared by isolating islet beta cells from the subject in need thereof. These isolated islet beta cells may comprise (e.g., be transfected, infected, etc. with) an expression vector comprising a nucleic acid sequence encoding the fugetactic agent (e.g., CXCL12, CXCL13). Alternatively, the beta cell may be genetically modified to express the endogenous fugetactic agent (e.g., CXCL12, CXCL13) gene such that it constitutively produces a fugetactic effective amount of the fugetactic agent (e.g., CXCL12, CXCL13).

In an embodiment of this invention the beta cells comprise (e.g., be transfected, infected, etc. with) an expression vector comprising a nucleic acid molecule that encodes the fugetactic agent (e.g., CXCL12, CXCL13), said nucleic acid molecule being in operable linkage with a promoter suitable for expression in the beta cells. The vector may integrate into the genome of the beta cell or it may exist episomally and not integrate into the genome.

The transgenic beta cells of the invention may also be prepared from an adult stem cell by isolating adult stem cells from the subject, culturing the stem cells under appropriate conditions to expand the population and to induce differentiation into beta cells. The cells may be modified to express fugetactic effective amounts of the fugetactic agent (e.g., CXCL12, CXCL13) by introducing into the cells an expression vector encoding fugetactic amounts of the fugetactic agent (e.g., CXCL12, CXCL13) or by editing the genome to express fugetactic amounts of the fugetactic agent (e.g., CXCL12, CXCL13). The vector may be introduced into the stem cells prior to differentiation into beta cells or the genome of the stem cells may be edited to contain the heterologous promoter. Alternatively, the vector may be introduced into the resulting beta cells or the genome of the resulting beta cells may be edited to contain the heterologous promoter.

The transgenic beta cells of the invention may also be prepared by generating induced pluripotent stem (iPS) cells from somatic cells, e.g., beta cells, fibroblasts or keratinocytes, of a subject; treating the iPS cells to induce differentiation into beta cells; and introducing into the differentiated beta cells an expression vector comprising a nucleic acid sequence encoding the fugetactic agent (e.g., CXCL12, CXCL13).

The transgenic beta cells of the invention may also be prepared by preparing induced pluripotent stem (iPS) cells generated from somatic cells of a subject; introducing into the iPS cells an expression vector comprising a nucleic acid sequence encoding the fugetactic agent (e.g., CXCL12, CXCL13); and treating the iPS cells, before or after introduction of the transgene, to induce differentiation into beta cells.

The transgenic beta cells of this invention may also be generated by obtaining progenitor cells or progenitor-like cells, e.g., pancreatic β-cell progenitors, introducing a vector comprising a nucleic acid sequence encoding the fugetactic agent (e.g., CXCL12, CXCL13) into the cells, and treating the cells either before or after introducing the vector to induce differentiation into beta cells, or insulin releasing cells responsive to glucose levels in the body, by methods known in the art, see e.g., Millman et al. Nature Communications (10 May 2016) page 1-8); Baek et al. Curr Stem Cell Rep (2016) 2:52-61; Russ et al., EMBO. J. 34, 1759-1772 (2015); and, Qadir el al., Cell Reports 22, 2408-2420 (Feb. 27, 2018). The progenitor cell and progenitor-like cells may be autologous or non-autologous, e.g., allogeneic, to the subject treated with the transgenic cells. Insulin-producing cells responsive to glucose levels in the body, (see e.g., Qadir et al., supra), may be genetically modified as described herein to express fugetactic levels of the fugetactic agent (e.g., CXCL12, CXCL13) and are also an embodiment of this invention. Such genetically modified insulin producing cells can likewise be used in the methods of this invention to treat diabetes as described herein.

Any suitable somatic cell from a subject may be reprogrammed into an iPS cell by methods known in the art, see e.g., Pagliuca and Melton (2013) How to make a functional R-cell, Development (3013) 140(12); 2472-2483; Yu et al. (2007). Induced pluripotent stem cell lines derived from human somatic cells. Science 318, 1917-1920; Takahashi and Yamanaka, 2006, Cell 126(4):663-676; Wernig et al., 2007, Nature 448:7151; Okita et al., 2007 Nature 448:7151; Maherali et al., 2007 Cell Stem Cell 1:55-70; Lowry et al., 2008 PNAS 105:2883-2888; Park et al., 2008 Nature 451: 141-146; Takahashi et al., 2007 Cell 131, 861-872; U.S. Pat. Nos. 8,546,140; 7,033,831 and; 8,268,620. The iPS cells may be differentiated into beta cells using methods known in the art, see e.g. US patent publication no. 20170081641 and US patent publication no 20130164787, and Millette and Georgia, "Gene Editing and Human Pluripotent Stem Cells: Tools for advancing Diabetes Disease Modeling and Beta Cell Development", Current Diabetes Reports November 2017, 17: 116; US patent application no. 20130273651; Shi, Y., et al. Stem Cells., 25: 656-662 (2005); or Tateishi, K., et al., J Biol Chem., 283: 31601-31607 (2008).

Preferably the fugetactic agent-encoding sequence is in operable linkage with a regulatory region that is suitable for expression in a beta cell. Suitable regulatory regions are known in the art, and include promoters such as, e.g., mammalian promoters including, e.g., hypoxanthine phosphoribosyl transferase (HPTR), adenosine deaminase, pyruvate kinase, β-actin promoter, muscle creatine kinase promoter, and human elongation factor promoter (EF1α), a GAPDH promoter, an actin promoter, and an ubiquitin promoter and viral promoters including SV40 early promoter, SV40 late promoter, metallothionein promoter, murine mammary tumor virus promoter, Rous sarcoma virus promoter, polyhedrin promoter, human immunodeficiency virus (HIV) promoters, cytomegalovirus (CMV) promoters, adenoviral promoters, adeno-associated viral promoters, or the thymidine kinase promoter of herpes simplex virus. Other relevant promoters, e.g., viral and eukaryotic promoters, are also well known in the art (see e.g., in Sambrook and Russell (Molecular Cloning: a laboratory manual, Cold Spring Harbor Laboratory Press). The regulatory region in operable linkage with the fugetactic agent-encoding sequence may be any constitutive promoter suitable for expression in the subject's cells.

The transgenic cells expressing the fugetactic agent (e.g., CXCL12, CXCL13) of this invention, whether autologous or non-autologous, e.g., allogeneic, may be administered to a subject in need thereof by any means known in the art for administering beta cells. The transgenic cells of this invention may be administered in an amount sufficient to provide levels of insulin able to alleviate at least some of the symptoms associated with low levels of insulin.

Another aspect of the invention is a method of treating diabetes in a subject in need thereof, comprising the steps of: (a) obtaining or deriving beta cells or insulin-producing beta-like cells, from the subject; (b) introducing a suitable expression vector encoding the fugetactic agent (e.g., CXCL12, CXCL13) into the cells to form autologous transgenic cells expressing the introduced the fugetactic agent (e.g., CXCL12, CXCL13); and (c) transplanting the autologous transgenic cells into the subject.

Many vectors useful for transferring exogenous genes into mammalian cells, e.g., beta cells, including vectors that integrate into the genome and vectors that do not integrate into the genome but exist as episomes, and methods for introducing such vectors into cells are available and known in the art. For example, retroviral vectors, lentiviral vectors, adenoviral vectors, adeno-associated (AAV)-based vectors and EBV-based vectors may be used. See, e.g., US 20110280842, Narayanavari and Izsvik, Cell Gene Therapy Insights 2017; 3(2), 131-158; Hardee et al., Genes 2107, 8, 65; Tipanee et al., Bioscience Reports (2017) 37, and Chira et al. Oncotarget, Vo. 6, No. 31, pages 30675-30703.

Another aspect of the invention is a method for promoting survival of beta cells in a biological sample comprising immune cells comprising introducing an expression vector encoding the fugetactic agent (e.g., CXCL12, CXCL13) into the beta cells, or by editing the genome of the beta cells such that the beta cells express fugetactic amounts of the fugetactic agent (e.g., CXCL12, CXCL13). In an aspect of this invention the fugetactic agent (e.g., CXCL12, CXCL13) is expressed by the beta cells at a level sufficient to block or inhibit migration of immune cells, e.g. T-cells, B-cells, and/or NK cells, to the beta cells. In an aspect of this invention the fugetactic agent (e.g., CXCL12, CXCL13) is expressed by the beta cells at a level sufficient to repel the immune cells from the beta cells. In an aspect of this invention the genetically modified beta cells are in a subject, e.g., a human subject having Type 1 or Type 2 diabetes. In one embodiment, the beta cells are autologous beta cells of the subject.

Methods for the delivery of viral vectors and non-viral vectors to mammalian cells are well known in the art and include, e.g., lipofection, microinjection, ballistics, virosomes, liposomes, immunoliposomes, polycation or lipid-nucleic acid conjugates, naked DNA, artificial virions, and agent-enhanced uptake of DNA. Lipofection reagents are sold commercially (e.g., Transfectam™ and Lipofectin™). Cationic and neutral lipids suitable for efficient receptor-recognition lipofection of polynucleotides are known. Nucleic acid can be delivered to cells (ex vivo administration) or to target tissues (in vivo administration). The preparation of lipid:nucleic acid complexes, including targeted liposomes such as immunolipid complexes, is well known to those of skill in the art. Recombination mediated systems can be used to introduce the vectors into the cells. Such recombination methods include, e.g., use of site specific recombinases like Cre, Flp or PHIC31 (see e.g. Oumard et al., Cytotechnology (2006) 50: 93-108) which can mediate directed insertion of transgenes.

Vectors suitable for use in this invention include expression vectors comprising a nucleic acid encoding a fugetactic agent (e.g., CXCL12, CXCL13) in operable linkage with a promoter to direct transcription. Suitable promoters are well known in the art and described, e.g., in Sambrook and Russell (Molecular Cloning: a laboratory manual, Cold Spring Harbor Laboratory Press). The promoter used to direct expression of the fugetactic agent (e.g., CXCL12, CXCL13) may be, e.g., example, SV40 early promoter, SV40 late promoter, metallothionein promoter, murine mammary tumor virus promoter, Rous sarcoma virus promoter, or other promoters shown to be effective for expression in mammalian cells.

Vectors useful in the methods of this invention include, e.g., SV40 vectors, papilloma virus vectors, Epstein-Barr virus vectors, retroviral vectors, and lentiviral vectors.

The vectors used in this invention may comprise regulatory elements from eukaryotic viruses, e.g., SV40, papilloma virus, and Epstein-Barr virus, including e.g., signals for efficient polyadenylation of the transcript, transcriptional termination, ribosome binding, and/or translation termination. Additional elements of the vectors may include, e.g., enhancers, and heterologous spliced intronic signals.

In an embodiment of this invention, the genome of the beta cell may be genetically modified to increase the expression levels of an endogenous fugetactic agent (e.g., CXCL12, CXCL13) gene. Such increased expression may be achieved by introducing a heterologous promoter in operable linkage with the endogenous fugetactic agent (e.g., CXCL12, CXCL13) gene or by altering the endogenous fugetactic agent (e.g., CXCL12, CXCL13) promoter such that the beta cell expresses a fugetactic level of fugetactic agent (e.g., CXCL12, CXCL13). Such increased expression may be achieved by introducing a promoter into the genome of the beta cell such that it is in operable linkage with the endogenous fugetactic agent-encoding sequence and thereby expresses or overexpresses the fugetactic agent in a fugetactic amount.

Gene editing technologies for modifying the genome are well known in the art and include e.g., CRISPR/CAS 9, Piggybac, Sleeping Beauty genome editing systems, (see for example, Zhang et al. Molecular Therapy Nucleic Acids, Vol 9, December 2017, page 230-241; systems (see e.g., Cong et al., Science. 2013; 339(6121): 819-23; Mali et al., Science. 2013; 339(6121): 823-6; Gonzilez et al., Cell Stem Cell. 2014; 15(2): 215-26); He et al., Nucleic Acids Res. 2016; 44(9); Hsu et al., Cell. 2014; 157(6): 1262-78.), zinc finger nuclease-based systems (see e.g., Porteus and Carroll, Nat Biotechnol. 2005; 23(8): 967-73; Urnov el al., Nat Rev Genet. 2010; 11(9): 636-46), TALEN-based systems (transcription activator-like effector nucleases)(see e.g., Cermak el al., Nucleic Acids Res. 2011; 39(12); Hockemeyer et al., Nat Biotechnol. 2011; 29(8): 731-4; Joung and Sander J D, Nat Rev Mol Cell Biol. 2013; 14(1): 49-55; Miller et al., Nat Biotechnol. 2011; 29(2): 143-8, and Reyon et al., Nat Biotechnol. 2012; 30(5): 460-5).

In one embodiment, the transgenic beta cells described herein are treated with an agent that renders the cells viable and capable of controlling blood sugar in a patient but unable to replicate (i.e., induced cellular senescence). One such agent is Mitomycin C that is a known DNA cross-linking agent. Upon treatment, the DNA in these cells is cross-linked thereby rendering impossible the formation of single stranded DNA necessary for replication. Such a treatment prevents the cells, especially those generated from stem cells, from dividing such that if the cell morphs into a cancer cell it cannot divide. Other known agents capable of inducing cellular senescence include those recited by Petrova, et al., "Small Molecule Compounds that Induce Cellular Senescence" Aging Cell, 15(6):999-1017 (2016) which reference is incorporated herein in its entirety. Such agents include, by way of example only, agents that cause telomere dysfunction due to replication-associated telomere shortening, subcytoxic stresses such as exposure to UV, gamma irradiation, hydrogen peroxide, and hypoxia. The specific means by which the beta cells of this invention are rendered non-replicative is not critical provided that these cells can be implanted without risk of cellular division. Studies show adult human pancreas has very little beta cell turnover, suggesting that limiting the ability of the cells to divide will have little to no effect on insulin production by implanted cells. See, e.g., Perl et al., *The Journal of Clinical Endocrinology & Metabolism*, Volume 95, Issue 10, 1 Oct. 2010, Pages E234-E239.

Another aspect of the invention is a method of modulating the levels of insulin in a subject, comprising administering to the subject in need thereof the beta cells of this invention wherein the beta cells express insulin and produce a fugetactic agent (e.g., CXCL12, CXCL13) in a fugetactic amount. The beta cells may be autologous beta cells or non-autologous beta cells, e.g. allogeneic beta cells, and may harbor a vector expressing the fugetactic agent, which vector may be integrated into the beta cell genome or exist episomally. In an embodiment of this invention the transgenic beta cells may be a genetically modified to overexpress endogenous fugetactic agent (e.g., CXCL12, CXCL13) at a fugetactic level.

Methods of introducing the transgenic beta cells described herein into individuals are well known to those of skills in the art and include, but are not limited to, injection, intravenous, intraportal, or parenteral administration. Single, multiple, continuous or intermittent administration can be effected. See e.g., Schuetz and Markmann, Curr Transplant Rep. 2016 September; 3(3): 254-263.

Pharmaceutically acceptable carriers include sterile aqueous solutions or dispersions and sterile powders for the extemporaneous preparation of sterile injectable solutions or dispersion. The use of media and agents for pharmaceutically active substances, including cells, is well known in the art. A typical pharmaceutical composition for intravenous infusion of beta cells could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18th and 19th editions thereof, which are incorporated herein by reference.

The transgenic and genetically modified beta cells of the invention can be introduced into any of several different sites well known in the art, including but not limited to the pancreas, the abdominal cavity, the kidney, the liver, the portal vein or the spleen of the subject.

In addition, in order to avoid any possible transformation of the transgenic beta cells into cancer cells that could result in the possibility of the patient developing a tumor, the transgenic beta cells can be rendered senescent by contacting with known agents such as Mitomycin C, or exposure to subtoxic stress from ionizing radiation, hypoxia, hydrogen peroxide, etc. Cells derived from pluripotent stem cells typically undergo apoptosis during inappropriate cell division or due to immune cell clearance. The senescent transgenic beta cells described herein are incapable of division thereby eliminating apoptotic triggers arising during cellular division. In addition, the senescent transgenic beta cells described herein are immune cell resistant thereby providing protection against apoptosis induction due to immune cell clearance. Accordingly, it is contemplated that the transgenic beta cells described herein will have a longer lifespan to a significantly longer lifespan than non-senescent transgenic beta cells.

The transgenic and preferably senescent modified beta cells may be transplanted into the subject via a graft. An ideal beta cell transplantation site would be one that supports the implantation, long-term function and survival of grafted cells in the subject and is easily accessible for maximal patient safety. Sites for implantation include the liver, intestinal, subdermal, and pancreatic sites.

The following abbreviations used herein have the following meanings and if abbreviations are not defined, they have their generally accepted scientific meaning. Amino acids are recited herein using their established one letter abbreviations.

| | |
|---|---|
| FLAG = | DYKDDDDK protein tag (SEQ ID NO: 10) |
| g/L = | grams per liter |
| HRP = | horseradish peroxidase |
| LDH = | lactate dehydrogenase |
| iBLOT = | Semi-dry protein transfer device (Invitrogen) |
| MES = | 2-(N-morpholino)ethanesulfonic acid |
| mL = | milliliter |
| N/A = | not applicable |
| nM = | nanomolar |
| PBMC = | peripheral blood mononuclear cells |
| PBS = | phosphate buffered saline |
| TMB = | 3,3',5,5'-Tetramethylbenzidine |
| μL = | microliters |
| μg = | micrograms |
| x g = | times gravity |

EXAMPLES

Example 1: Model Cells Used to Assess Expression Levels of CXCL12-a and -b Isoforms HEK293 cells were transfected with 2 different isoforms of CXCL12 (alpha and beta) using commercially available plasmids for each isoform (plasmids available from GenScript). Transfected cells were selected with 250 ug/mL of G418 (commercially available from ThermoFisher) and a stable pool for each isoform was created. Cells were allowed to condition a suitable medium for 3 days. Conditioned medium from the transfected HEK293 cells expressing CXCL12 alpha and CXCL12 beta were diluted 1:1 with assay dilution buffer. Two separate pools were established for each isoform and then the concentration of each isoform in solution were obtained by absorption using a standardized concentration curve. This experiment was repeated twice and the results are as follows:

| | CXCL12 alpha | CXCL12 beta |
|---|---|---|
| 1. | 310 nM | 1410 nM |
| 2. | 274 nM | 1330 nM |

The above results evidence that transgenic model cells express CXCL12 beta at significantly higher levels than transgenic model cells that express CXCL12 alpha.

Example 2—Model Cells Used to Assess Expression Levels of Other Isoforms of CXCL12

HEK293 cells were transfected with 5 different isoforms of CXCL12 (alpha and beta) using commercially available plasmids for each isoform (plasmids available from GenScript). Transfected cells were selected with 250 ug/mL of G418 (commercially available from ThermoFisher) and a stable pool for each isoform was created. Cells were allowed to condition in a suitable medium for 3 days. The conditioned medium was separated in a 4-8% NuPage gel (commercially available from ThermoFisher) with MES buffer and transferred to nitrocellulose (iBLOT).

Expression levels were detected with HRP labeled, anti-FLAG tag antibody/TMB chromogen (available from GenScript) on a Western Blot, as shown in FIG. 1. The results evidenced that the gamma, delta and theta isoforms of CXCL12 had greater concentrations than the alpha or beta isoforms.

Example 3: Preparation of Transgenic Beta Cells

Pancreatic beta cells derived from human induced pluripotent stem cells were purchased from Takara Bio USA, Inc. (Mountain View, Calif.) and cultured according to provided instructions.

Cells were transduced with lentiviral vectors (pLenti-C-Myc-DDK, OriGene Technologies, Rockville, Md.) containing a human CXCL12 isotype (CXCL12a/SDF-1alpha or CXCL12b/SDF-1beta) or control. The lentiviral vectors were used at a ratio of about 10:1 per beta cell. The sequences, including the tag (underlined) are provided below. Concentration of the CXCL12 isotype was determined by ELISA (RayBioTech, Norcross, Ga.) (Table 1).

CXCL12a (aka SDF1a)

SEQ ID NO.: 9

Accession No. NM_199168

ATGAACGCCAAGGTCGTGGTCGTGCTGGTCCTCGTGCTGACCGCGCT

CTGCCTCAGCGACGGGAAGCCCGTCAGCCTGAGCTACAGATGCCCAT

GCCGATTCTTCGAAAGCCATGTTGCCAGAGCCAACGTCAAGCATCTC

-continued
AAAATTCTCAACACTCCAAACTGTGCCCTTCAGATTGTAGCCCGGCT

GAAGAACAACAACAGACAAGTGTGCATTGACCCGAAGCTAAAGTGGA

TTCAGGAGTACCIGGAGAAAGCTTTAAACAAGACGCGTACGCGGCCG

CTCGAGCAGAAACTCATCTCAGAAGAGGATCTGGCAGCAAATGATAT

CCTGGATTACAAGGATGACGACGATAAGGTTTAA

CXCL12b (aka SDF1b)
SEQ ID NO.: 8
Accession No. NM_000609
ATGAACGCCAAGGTCGIGGICGTGCTGGTCCTCGTGCTGACCGCGCTCT

GCCTCAGCGACGGGAAGCCCGTCAGCCTGAGCTACAGATGCCCATGCCG

ATTCTTCGAAAGCCATGTTGCCAGAGCCAACGTCAAGCATCTCAAAATT

CTCAACACTCCAAACTGTGCCCTTCAGATTGTAGCCCGGCTGAAGAACA

ACAACAGACAAGTGTGCATTGACCCGAAGCTAAAGTGGATTCAGGAGTA

CCTGGAGAAAGCTTTAAACAAGAGGTTCAAGATGACGCGTACGCGGCCG

CTCGAGCAGAAACTCATCTCAGAAGAGGATCTGGCAGCAAATGATATCC

TGGATTACAAGGATGACGACGATAAGGTTTAA

Example 4: Transgenic Beta Cells Repel PBMCs

The transgenic beta cells from Example 3 were contacted with human peripheral blood mononuclear cells (PBMCs, Innovative Research, Novi, Mich.) at a ratio of 30:1 (PBMCs to beta cell). Briefly, PBMCs were resuspended in beta full culture medium, counted and adjusted to allow for a 30:1 PBMC:beta cell ratio with addition of 100 uL of PBMCs (to minimize dilution of the expressed CXCL12). Final volume was 1.1 mL. Background controls of beta cells without PBMCs and PBMCs without beta cells were also created. Immediately 150 uL of medium was removed from each sample and centrifuged at 1200×g for 10 minutes. Supernatant was removed and stored at 4° C. (time zero). Cells were returned to the incubator and sampled in a similar way to the time zero sample at both 24 and 48 hours later.

Release of LDH was tested at 24 and 48 hours after contact using Pierce LDH Cytotoxicity Assay Kit (Thermo Scientific) according to manufacturer's instructions. Increased LDH is an indicator of cytotoxicity (cell lysis).

Figure 2A:
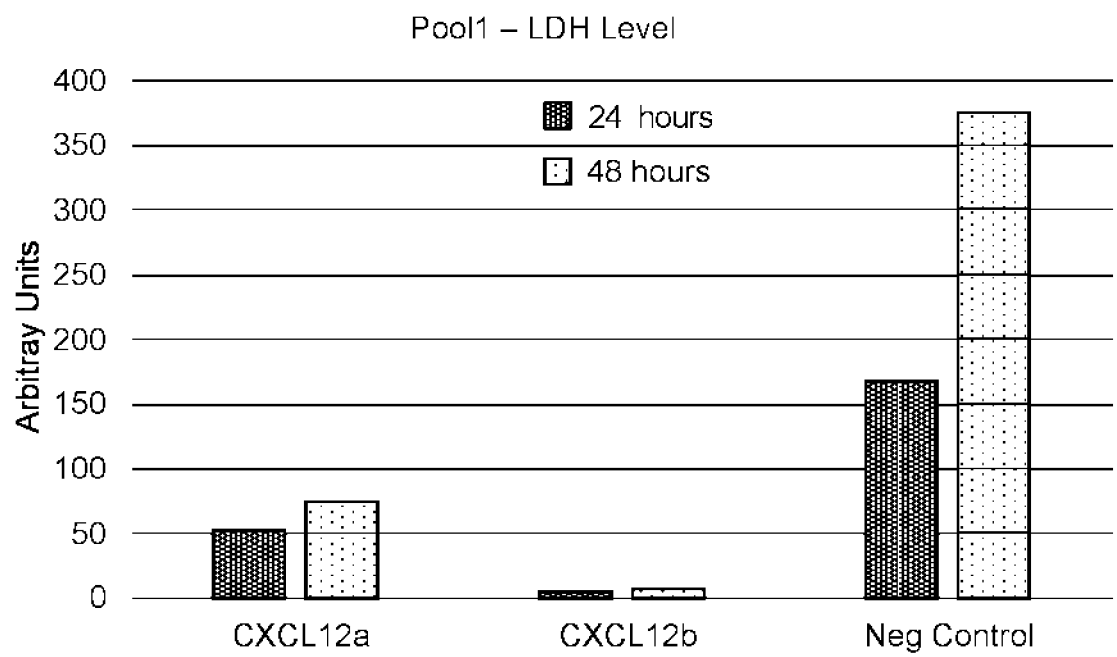
FIGS. 2A and 2B are bar graphs showing the relative amount of lactate dehydrogenase (LDH, a marker of cell lysis) released from CXCL12alpha- or CXCL12beta-expressing beta cells incubated with PBMCs at a 30:1 PBMC:beta cell ratio for 24 and 48 hours.
Figure 2B:
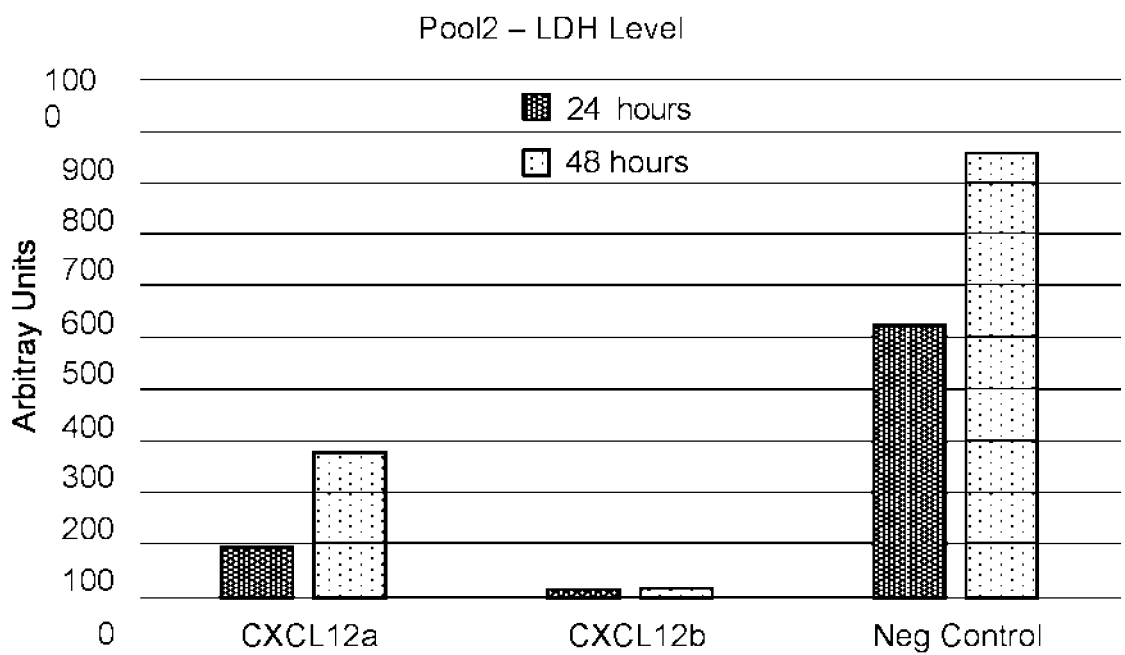

Data (background subtracted) from a representative experiment are provided in Table 2 and FIG. 2A. Data from a second representative experiment are provided in FIG. 2B.

TABLE 2

LDH and CXCL12 Levels

| Cytokine | LDH - 24 hr | LDH - 48 hr | Cytokine Conc. |
| --- | --- | --- | --- |
| Control | 170 | 375 | N/A |
| SDF1a | 52 | 75 | ~100 nM |
| SDF1b | 4 | 7 | ~400 nM |

These data indicate that expression of CXCL12 by beta islet cells protects the beta islet cells from immune cell attack thereby rendering them resistant. Beta cells expressing SDF1b/CXCL12b, which was expressed at a higher level than SDF1a/CXCL12a in this experiment, shows essentially no cytotoxicity in the presence of PBMCs.

Example 5: Alternative Preparation of Transgenic Beta Cells

Beta cells are isolated from a subject having type 1 diabetes are transfected or infected in vitro with a retroviral expression vector encoding CXCL12 or a control retroviral vector that does not encode CXCL12. Transgenic beta cells harboring the retroviral vector encoding CXCL12 are assayed for expression of fugetactic amounts of CXCL12 using a Boyden chamber assay as previously described in Poznansky et al., Journal of Clinical Investigation, 109, 1101 (2002). It is expected that transgenic beta cells expressing at least 100 nM CXCL12 will repel immune cells in this assay.

Example 6: Effect of Forced Senescence of Transgenic Beta Cells on Transgenic Cytokine Expression Beta cells were prepared as described in Example 3. Expression levels of SDF1a/CXCL12a and SDF1b/CXCL12b were assayed by ELISA before Mitomycin C (available from Santa Cruz Biotechnology) treatment to determine baseline expression ("Before"). Medium was replaced with fresh medium containing 10 ug/mL Mitomycin C—an agent known to induce senescence. Cells were returned to the incubator for 2 hours. The mitomycin C containing medium was removed by gentle pipetting. The cells were washed with PBS twice. After the second wash, the cells were fed fresh complete medium. SDF1a/CXCL12a or SDF1b/CXCL12b expression was determined by ELISA assay.

Figure 3:
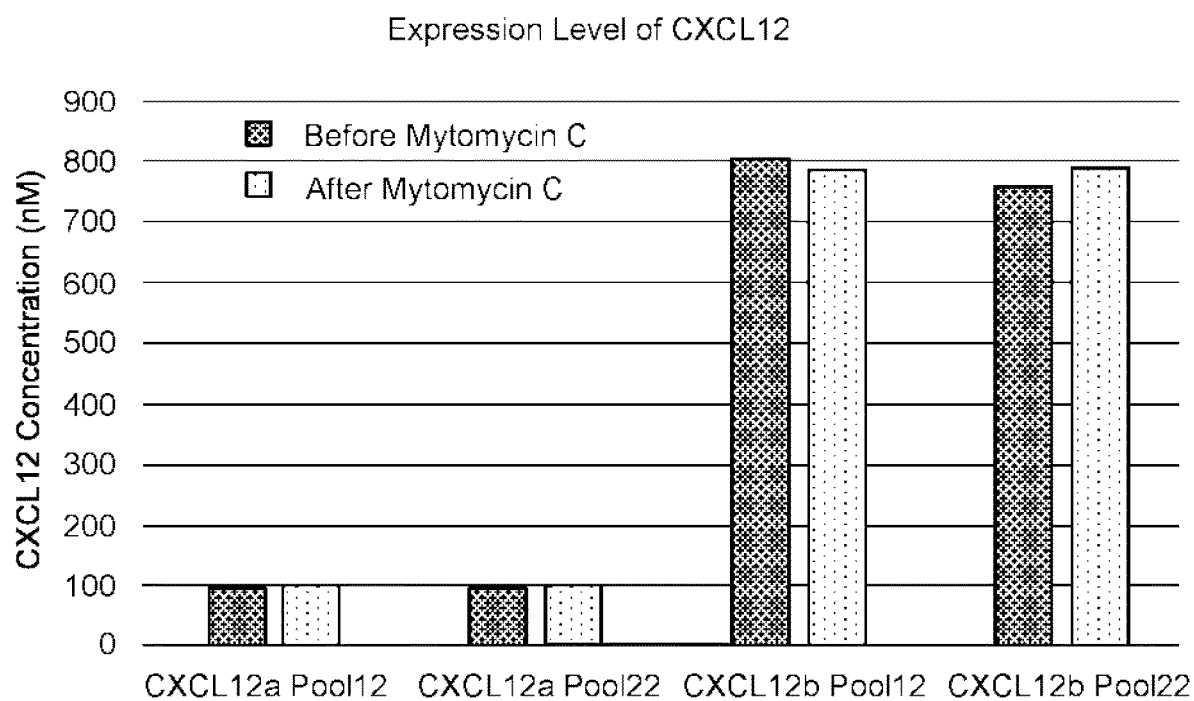
FIG. 3 shows the level of expression of CXCL12alpha and CXCL12beta in two sets of beta cells expressing each cytokine.

Data from two representative experiments are shown in Table 3 and FIG. 3A. SDF1a/CXCL12a and SDF1b/CXCL12b expression is not affected by forced senescence of the transgenic beta cells.

TABLE 3

CXCL12a and -b levels before and after Mitomycin C treatment

| Cytokine | Before Mitomycin C | After Mitomycin C |
| --- | --- | --- |
| CXCL12a Pool 12 | 97.5 nM | 100.5 nM |
| CXCL12a Pool 22 | 98.2 nM | 99.4 nM |
| CXCL12b Pool 12 | 806.2 nM | 789.3 nM |
| CXCL12b Pool 22 | 757.1 nM | 788.0 nM |

Example 7: Effect of Forced Senescence of Transgenic Beta Cells on PBMC Challenge Beta cells were prepared as described in Example 3. Cells were treated with Mitomycin C or control as described in Example 4. Cells were contacted with PBMCs as described in Example 2.

Figure 4A:
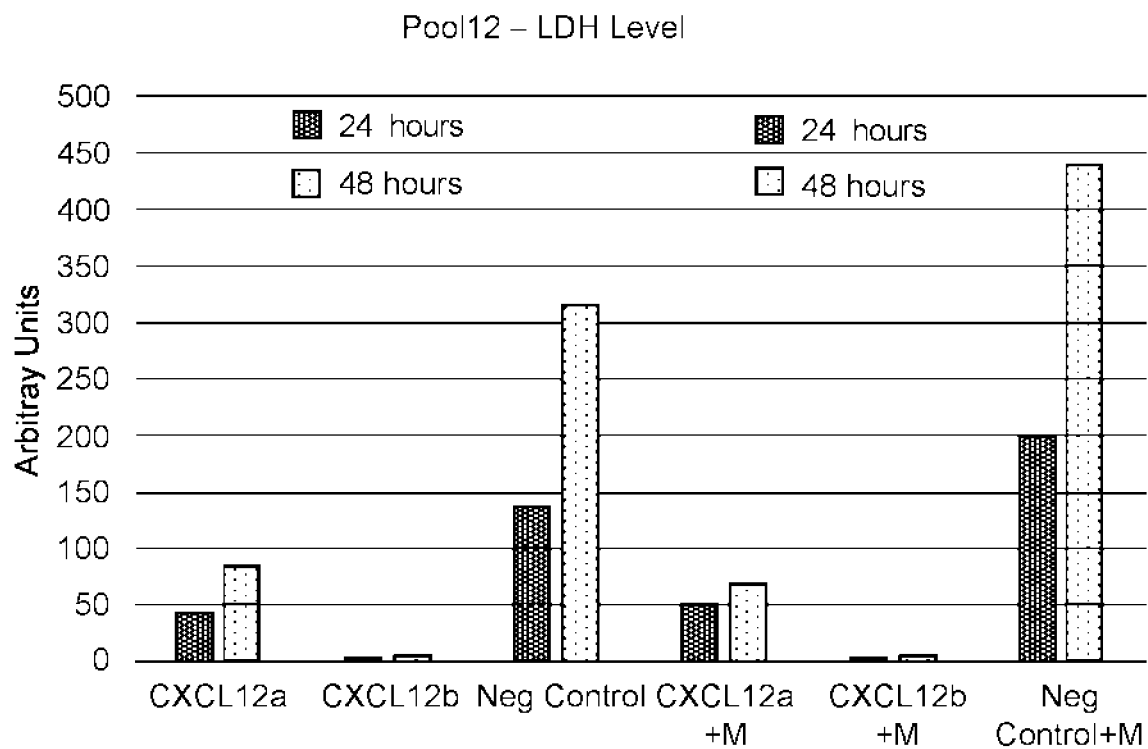
FIGS. 4A and 4B are bar graphs showing the relative amount of LDH released from CXCL12alpha- or CXCL12beta-expressing beta cells incubated with PBMCs at a 30:1 PBMC:beta cell ratio for 24 and 48 hours, with or without induced senescence of the beta cells (by mitomycin C treatment).
Figure 4B:
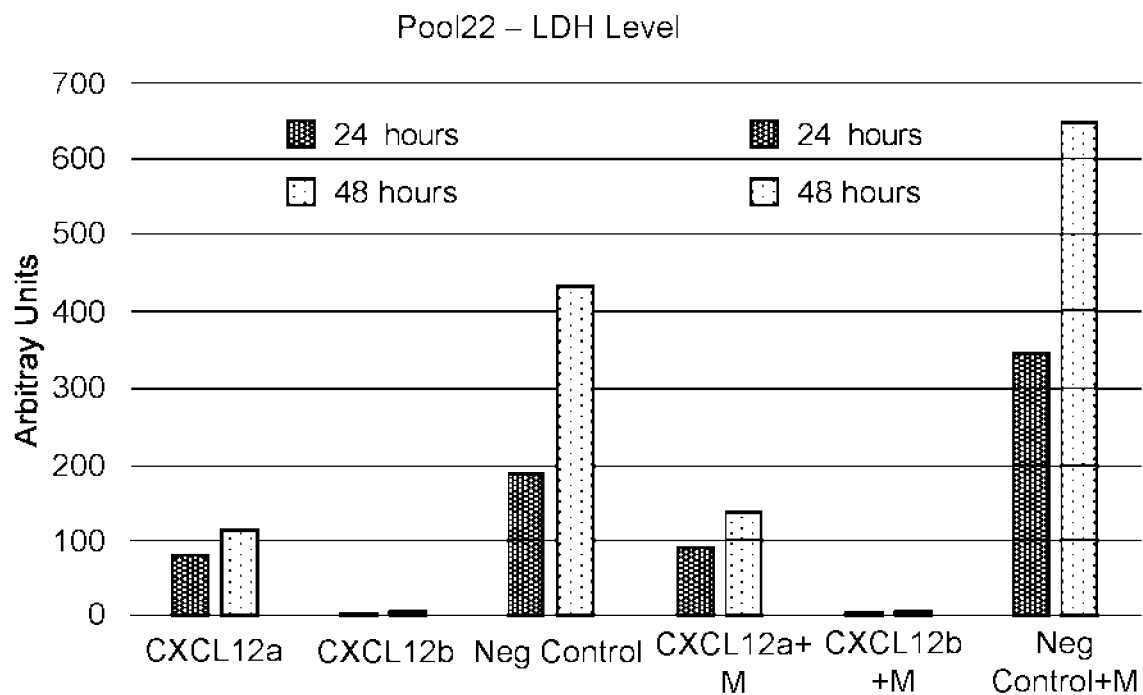

Data from two representative experiments are shown in FIGS. 4A and 4B. LDH levels are not affected by forced senescence of the transgenic beta cells.

Example 8: Effect of Forced Senescence of Transgenic Beta Cells on Insulin Production Beta cells were prepared as described in Example 3. Cells were treated with Mitomycin C or control as described in Example 4.

Full growth medium was replaced with 1 mL of Medium 2 and maintained on Medium 2 for 2 days with medium replacement every 24 hours. On day 3, the beta cells were challenged with the hyperglycemic medium (4.5 g/L glucose). Samples of conditioned media were taken 24 hours following hyperglycemic challenge and insulin expression was measured by sandwich ELISA.

Figure 5:
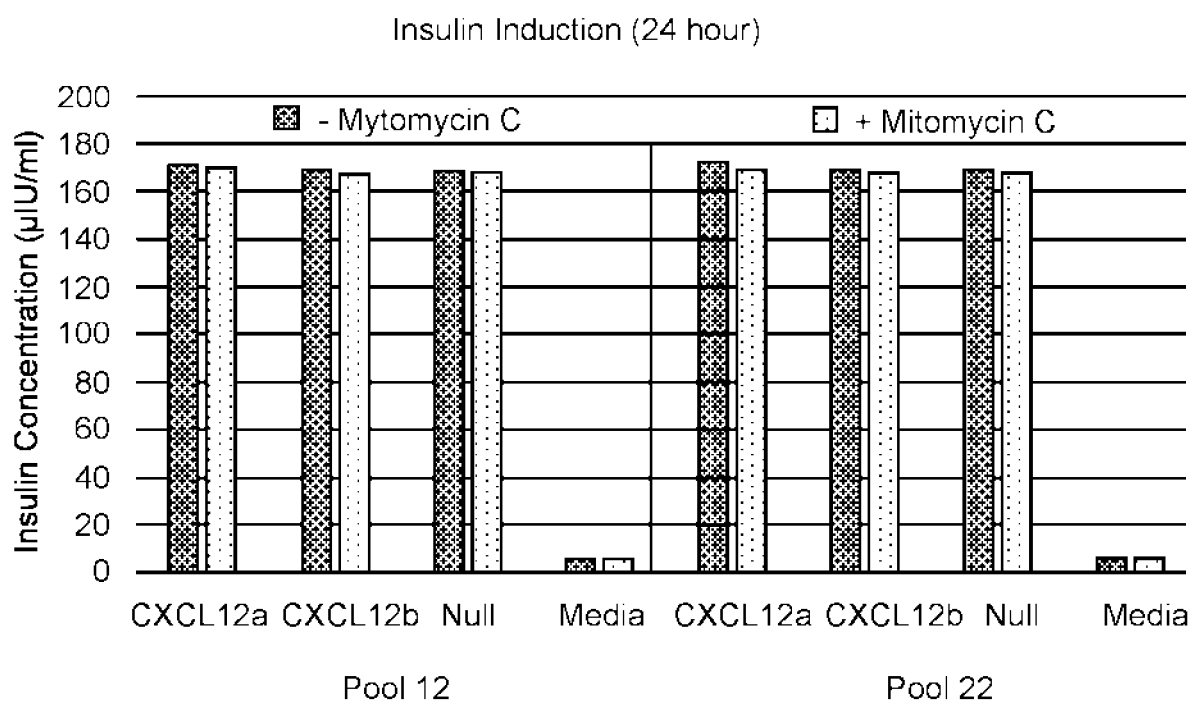
FIG. 5 shows insulin induction by hyperglycemic challenge of beta cells expressing CXCL12alpha or CXCL12beta, with or without treatment with mitomycin C.

Data from two representative experiments are shown in Table 3 and FIG. 5. The results evidence that transgenic beta cells and transgenic senescent beta cells produced substantially equal amounts of insulin as the control beta cells in response to hyperglycemic challenge.

TABLE 3

Insulin Expression in response to hyperglycemic challenge

| Sample | Before Mytomycin C | After Mytomycin C |
|---|---|---|
| CXCL12a Pool 12 | 170.9 mIU/ml | 170.0 mIU/ml |
| CXCL12a Pool 22 | 172.3 mIU/ml | 169.5 mIU/ml |
| CXCL12b Pool 12 | 169.6 mIU/ml | 167.4 mIU/ml |
| CXCL12b Pool 22 | 169.6 mIU/ml | 168.1 mIU/ml |
| No cytokine Pool 12 | 168.3 mIU/ml | 168.2 mIU/ml |
| No cytokine Pool 22 | 168.9 mIU/ml | 167.9 mIU/ml |
| No hyperglycemic Pool 12 | 6.04 mIU/ml | 5.97 mIU/ml |
| No hyperglycemic Pool 22 | 6.70 mIU/ml | 6.36 mIU/ml |

Example 9: In Vivo Evaluation of Transgenic Beta Cells

Humanized mice having a humanized immune system, see e.g., N. Walsh, "Humanized mouse models of clinical disease," Annu Rev Pathol 2017, 12, 187-215; E. Yoshihara et al., are administered either the transgenic human beta cells expressing fugetactic amounts of CXCL12 or the control transgenic human beta cells and the production of insulin and survival of the transgenic beta cells in the mice are assayed at various time points after the initial administration. It is contemplated that the transgenic human beta cells expressing fugetactic amounts of CXCL12 will survive for longer periods than the control transgenic human beta cells. It is also contemplated that the mice receiving the transgenic beta cells expressing fugetactic amounts of CXCL12 will also have higher amounts of human insulin than mice receiving the control transgenic human beta cells and the higher levels of human insulin will persist for longer periods of time as compared to the levels in mice administered the control transgenic human beta cells.

Humanized mice having a humanized immune system, see e.g., N. Walsh, "Humanized mouse models of clinical disease," Annu Rev Pathol 2017, 12, 187-215; E. Yoshihara et al., are administered either genetically modified human beta cells overexpressing CXCL12 from an endogenous CXCL12 gene, or control human beta cells and the production of human insulin and survival of the beta cells in the mice are assayed at various time points after the initial administration. It is contemplated that the genetically modified human beta cells overexpressing CXCL12 will survive for longer periods than the control human beta cells that were not genetically modified to overexpress CXCL12. It is also contemplated that mice receiving the genetically modified human beta cells overexpressing CXCL12 will also have higher amounts of human insulin than mice receiving the control human beta cells and the higher levels of human insulin will persist for longer periods of time as compared to the levels in mice administered the control human beta cells.

Optionally, the cells are treated with an agent that cross-links the DNA within the cell to prevent cell division (e.g., Mitomycin C).

The foregoing description has been set forth merely to illustrate the invention and is not meant to be limiting. Since modifications of the described embodiments incorporating the spirit and the substance of the invention may occur to persons skilled in the art, the invention should be construed broadly to include all variations within the scope of the claims and equivalents thereof.

The invention claimed is:

1. A population of isolated genetically engineered human beta cells comprising a nucleic acid encoding for exogenous or heterologous expression of a human CXCL12 protein isoform such that said population of said cells is characterized as encoding for the expression of a fugetactic amount of said CXCL12 protein isoform and is therefore resistant to cell death when in the presence of human immune cells in vitro as compared to a population of unengineered human beta cells obtained from a human stem cell that has been differentiated ex vivo into human beta cells,
- wherein the nucleic acid is operably linked to an exogenous promoter,
- wherein the population of genetically engineered human beta cells is insulin producing and has been exposed to a senescence inducing agent, and
- wherein said population of genetically engineered human beta cells is obtained from a human stem cell that has been differentiated ex vivo into a human beta cell and is either autologous or allogeneic.

2. The population of isolated human beta cells of claim 1, wherein the differentiated human beta cell is allogeneic.

3. The population of isolated human beta cells of claim 1,
- wherein said fugetatic characterization is based on the relative amounts of lactate dehydrogenase (LDH) measured after assaying said population of engineered cells for 48 hours in the presence of human peripheral blood mononuclear cells (PBMCs) at a ratio of 1:30 genetically engineered beta cells to PBMCs; and
- wherein the amount of LDH is decreased by at least 50% for said population of engineered human beta cells compared to that of a population of unengineered human beta cells and 95% of the engineered human beta cells survive after 48 hours of exposure to PBMCs.

* * * * *

SEQUENCE LISTING

```
<160> NUMBER OF SEQ ID NOS: 10

<210> SEQ ID NO 1
<211> LENGTH: 89
<212> TYPE: PRT
<213> ORGANISM: Homo sapiens

<400> SEQUENCE: 1

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 2
<211> LENGTH: 93
```

<212> TYPE: PRT
<213> ORGANISM: Homo sapiens

<400> SEQUENCE: 2

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 3
<211> LENGTH: 119
<212> TYPE: PRT
<213> ORGANISM: Homo sapiens

<400> SEQUENCE: 3

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Arg Gln Lys Lys Arg Lys
            100                 105                 110

Ala Ala Gln Lys Arg Lys Asn
        115

<210> SEQ ID NO 4
<211> LENGTH: 140
<212> TYPE: PRT
<213> ORGANISM: Homo sapiens

<400> SEQUENCE: 4

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn Leu Ile Ser Ala Ala Pro Ala

```
                    85                  90                  95
Gly Lys Arg Val Ile Ala Gly Arg Ala Leu His Pro Ser Pro Pro
                100                 105                 110

Arg Ala Cys Pro Thr Ala Arg Ala Leu Cys Glu Ile Arg Leu Trp Pro
            115                 120                 125

Pro Pro Glu Trp Ser Trp Pro Ser Pro Gly Asp Val
        130                 135                 140

<210> SEQ ID NO 5
<211> LENGTH: 90
<212> TYPE: PRT
<213> ORGANISM: Homo sapiens

<400> SEQUENCE: 5

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn Cys
                85                  90

<210> SEQ ID NO 6
<211> LENGTH: 100
<212> TYPE: PRT
<213> ORGANISM: Homo sapiens

<400> SEQUENCE: 6

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Ile Trp Leu Tyr Gly Asn Ala
                85                  90                  95

Glu Thr Ser Arg
            100

<210> SEQ ID NO 7
<211> LENGTH: 109
<212> TYPE: PRT
<213> ORGANISM: Homo sapiens

<400> SEQUENCE: 7

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30
```

```
Cys Arg Cys Val Gln Glu Ser Ser Val Phe Ile Pro Arg Arg Phe Ile
         35                  40                  45

Asp Arg Ile Gln Ile Leu Pro Arg Gly Asn Gly Cys Pro Arg Lys Glu
         50                  55                  60

Ile Ile Val Trp Lys Lys Asn Lys Ser Ile Val Cys Val Asp Pro Gln
 65                  70                  75                  80

Ala Glu Trp Ile Gln Arg Met Met Glu Val Leu Arg Lys Arg Ser Ser
                 85                  90                  95

Ser Thr Leu Pro Val Pro Val Phe Lys Arg Lys Ile Pro
            100                 105

<210> SEQ ID NO 8
<211> LENGTH: 375
<212> TYPE: DNA
<213> ORGANISM: Homo sapiens

<400> SEQUENCE: 8
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga gaacaacaa cagacaagtg tgcattgacc cgaagctaaa gtggattcag      240
gagtacctgg agaaagcttt aaacaagagg ttcaagatga cgcgtacgcg gccgctcgag     300
cagaaactca tctcagaaga ggatctggca gcaaatgata tcctggatta caaggatgac     360
gacgataagg tttaa                                                      375

<210> SEQ ID NO 9
<211> LENGTH: 363
<212> TYPE: DNA
<213> ORGANISM: Homo sapiens

<400> SEQUENCE: 9
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga gaacaacaa cagacaagtg tgcattgacc cgaagctaaa gtggattcag      240
gagtacctgg agaaagcttt aaacaagacg cgtacgcggc cgctcgagca gaaactcatc     300
tcagaagagg atctggcagc aaatgatatc ctggattaca aggatgacga cgataaggtt     360
taa                                                                   363

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Tyr Lys Asp Asp Asp Asp Lys
 1               5
```